(12) United States Patent
Carroll

(10) Patent No.: US 6,375,634 B1
(45) Date of Patent: Apr. 23, 2002

(54) APPARATUS AND METHOD TO ENCAPSULATE, KILL AND REMOVE MALIGNANCIES, INCLUDING SELECTIVELY INCREASING ABSORPTION OF X-RAYS AND INCREASING FREE-RADICAL DAMAGE TO RESIDUAL TUMORS TARGETED BY IONIZING AND NON-IONIZING RADIATION THERAPY

(75) Inventor: Robert G. Carroll, Largo, FL (US)

(73) Assignee: Oncology Innovations, Inc., Largo, FL (US)

( * ) Notice: Subject to any disclaimer, the term of this patent is extended or adjusted under 35 U.S.C. 154(b) by 0 days.

(21) Appl. No.: 09/286,516

(22) Filed: Apr. 6, 1999

Related U.S. Application Data

(63) Continuation-in-part of application No. 09/195,056, filed on Nov. 18, 1998.
(60) Provisional application No. 60/066,195, filed on Nov. 19, 1997.

(51) Int. Cl.[7] ............................. A61N 1/30; A61F 13/20; A61B 18/18; A61B 17/00
(52) U.S. Cl. ............................. 604/19; 604/13; 606/41; 606/1
(58) Field of Search ........................ 514/2, 54; 606/41, 606/1; 604/13, 19; 424/93.21; 433/224

(56) References Cited

U.S. PATENT DOCUMENTS

| | | | |
|---|---|---|---|
| 4,280,954 A | | 7/1981 | Yannas et al. |
| 5,246,726 A | | 9/1993 | Horrobin et al. |
| 5,326,264 A | * | 7/1994 | Al Kasem |
| 5,427,767 A | | 6/1995 | Kresse et al. |
| 5,458,127 A | | 10/1995 | Unger et al. |
| 5,458,597 A | | 10/1995 | Edwards et al. |
| 5,472,441 A | | 12/1995 | Edwards et al. |
| 5,520,916 A | | 5/1996 | Dorigatti et al. |
| 5,622,946 A | | 4/1997 | Sessler et al. |
| 5,807,581 A | | 9/1998 | Rosenblatt et al. |
| 5,814,091 A | | 9/1998 | Dahlberg et al. |
| 5,908,623 A | | 6/1999 | Baetge et al. |
| 5,993,374 A | | 11/1999 | Kick |
| 6,015,541 A | | 1/2000 | Greff et al. |
| 6,022,866 A | | 2/2000 | Falk et al. |
| 6,090,063 A | | 7/2000 | Makower et al. |

FOREIGN PATENT DOCUMENTS

EP   0 380 370   *   8/1990

OTHER PUBLICATIONS

Anghileri, "Soft Tissue Calcification Induced by Iron Complexes," Calcified Tissue International, 51:83–84, 1992.

Anonymous, "Surgical and Minimally Invasive Therapies for BPH," Harvard Men's Health Watch, vol. 3, No. 1, Aug. 1998.

Aruoma et al., "Copper–ion–dependent damage to the bases in DNA in the presence of hydrogen peroxide," Biochem. J., 273:601–604, 1991.

Aruoma et al., "Damage to the Bases in DNA Induced by Hydrogen Peroxide and Ferric Iron Chelates," Journal of Biochemistry, 264(34):20509–12, 1989.

Castilho et al., "Oxidative Damage of Mitochondria Induced by Fe(II)citrate is Potentiated by a $Ca^{2+}$ and Includes Lipid Peroxidation and Alterations in Membrane Proteins," Archives of Biochemistry and Biophysics, vol. 308, No. 1, pp. 158–163, 1994.

Fujii et al., "Site–Specific Mechanisms of Initiation by Chelated Iron and Inhibition by α–Tocopherol of Lipid Peroxide–Dependent Lipid Peroxidation in Charged Micelles," Archives of Biochemistry and Biophysics, 284, No. 1, pp. 120–126, Jan. 1991.

Goldstein et al., "Transition Metal Ions and Oxygen Radicals," International Review on Experimental Pathology, vol. 31, pp. 133–165, 1990.

Gutteridge, "Ferrous–salt–promoted damage to deoxyribose and benzoate," Biochemistry Journal, 243:709–714, 1987.

Joy et al., "High–Efficiency of Ferricenium Salts as Radiosensitizers of V79 Cells in Vitro and the KHT Tumor In Vivo," International Journal of Radiation Oncology, Biology, Physics, 16(4):1053–1056, 1989.

Kapteijn et al., "Localizing the Sentinel Node in Cutaneous Melanoma: Gamma Probe Detection Versus Blue Dye," Annals of Surgical Oncology, 4(2) pp. 156–160, Mar. 1997.

Kapteijn et al., "Validation of Gamma Probe Detection of the Sentinel Node in Melanoma," The Journal of Nuclear Medicine, vol. 38, No. 3, Mar. 1997.

Lesnefsky et al., "Tissue Iron Overload and Mechanisms of Iron–Catalyzed Oxidative Injury," Free Radicals in Diagnostic Medicine, pp. 129–146 (Plenum Press 1994).

Nelson et al., "Enhanced X–ray sensitivity from excess ferriton iron," Cell Proliferation 411 (1991).

Nelson et al., "Ferritin–iron increases killing of Chinese hamster ovary cells by X–irradiation," Cell Prolif., 25:579–585, 1992.

Okada, "Iron–induced tissue damage and cancer: The role of reactive oxygen species–free radicals," Pathology International, 46:311–322, 1996.

(List continued on next page.)

Primary Examiner—Anthony C. Caputa
Assistant Examiner—Gary B. Nickol
(74) Attorney, Agent, or Firm—Caesar, Rivise, Bernstein, Cohen & Pokotilow, Ltd.

(57) ABSTRACT

Methods for conducting an operation on a living organism are provided, including methods in which a channel is provided around a tissue of the organism, and an encapsulating composition is infused into the channel to encapsulate the tissue in a capsule. The capsule impedes materials encapsulated therein from migrating to other tissues outside the capsule. Also provided are apparatuses for performing methods of the invention. In addition, an improved method of radiation therapy, in which a locally persistent radiation enhancing agent, such as iron dextran or colloidal chromic phosphate P-32, is administered in or near a tissue to be treated, is provided. The methods and apparatuses are especially useful in the treatment and removal of tumors.

21 Claims, 2 Drawing Sheets

OTHER PUBLICATIONS

Quinlan et al., Action of lead (II) and aluminum (III) ions of iron-stimulated lipid peroxidation in liposomes, erythrocyes and rat liver microsomal fractions, Biochemica et Biophysica Acta, 962:196–200, 1988.

Schaich et al., "Fenton Reactions in Lipid Phases[1]," Lipids 23(6):570–79, 1988.

Stevens et al., "Iron, Radiation, and Cancer," Enviromental Health Perspectives, vol. 87, pp. 291–300, 1990.

Suggs et al., "Preparation and characterization of poly (propylene fumarate–co–ethylene glycol) hydrogels," J. Biomater. Sci. Polymer Edn, vol. 9, No. 7, pp. 653–666, 1998.

Suslick et al., "On the origin of sonoluminescence and sonochemistry," Ultrasonics 28(5), pp. 280–290, Sep. 1990.

Teicher et al., "Some Complexes of Cobalt (III) and Iron (III) Are Radiosensitizers of Hypoxic EMT6 Cells[1]," Radiation Research 109:36–46, 1987.

Toyokuni, "Iron–Induced Carcinogenesis: The Role of Redox Regulation," Free Radical Biology & Medicine, vol. 20, No. 4, pp. 553–566, 1996.

Weinberg, "The role of iron in cancer," European Journal of Cancer Prevention, 5:19–36, 1996.

West et al., "Comparison of covalently and physically cross–linked polyethylene glycol–based hydrogels for the prevention of postoperative adhesions in a rat model," Biomaterials, vol. 16, No. 15, pp. 1153–1156, 1995.

Zocchi, "Ultrasonic Liposculpturing," Aesthetic Plastic Surgery, 16:287–298, 1992.

Buettner et al., "Catalytic Metals, Ascorbate and Free Radicals: Combinations to Avoid," Radiation Res. 145:532–41 (1996).

Cantoni et al., "Cytotoxic Impact of DNA Single vs. Double Strand Breaks in Oxidatively Injured Cells," Arch. Toxicol. Suppl., 1996, 18:223–35.

Chevion, "A site–specific mechanism for free radical induced biological damage: The essential role of redox–active transition metals," Free Radicals in Biology and Medicine, vol. 5:27–37, 1988.

K. Umezawa, "Induction of apoptosis in human pancreatic carcinoma cells by a synthetic bleomycin–like ligand," 89(9) Jpn. J. Cancer Res 947–53, Sep. 1998.

Reid, MD et al., "Perioperative Stimulation of Residual Cancer Cells Promotes Local and Distant Recurrence of Breast Cancer," 1997, American College of Surgeons, pp. 290–306.

Wardman, Peter, "Radiation chemistry: basic, strategic or tactical science?" pp. 175–190, Int. J. Radiat. Biol., 1989, vol. 55, No. 2.

Hoekstra, "Hyaluronan–Modified Surfaces for Medical Devices," Medical Device and Diagnostic Industry, pp. 48–58, Feb. 1999.

Lum, MD, "T Cell–Based Immunotherapy For Cancer: A Virtual Reality?," pp. 74–100, CA–A Cancer Journal of Clinicians, vol. 49, No. 2, Mar./Apr. 1999.

Morton et al., "Cytoreductive Surgery and Adjuvant Immunotherapy: A New Management Paradigm for Metastatic Melanoma," pp. 101–116. CA—A Cancer Journal of Clinicians, vol. 49, No. 2 Mar./Apr. 1999.

Rosenberg, MD, PhD., "A New Era of Cancer Immunotherapy: Converting Theory to Performance," pp. 70–73, CA–A Cancer Journal For Clinicians, vol. 49, No. 2 Mar./Apr. 1999.

Tjoa, PhD. et al., "Dendritic Cell–Based Immunotherapy for Prostate Cancer," pp. 117–128, CA—A Cancer Journal for Clinicians, vol. 49, No. 2, Mar./Apr. 1999.

* cited by examiner

APPARATUS AND METHOD TO ENCAPSULATE, KILL AND REMOVE MALIGNANCIES, INCLUDING SELECTIVELY INCREASING ABSORPTION OF X-RAYS AND INCREASING FREE-RADICAL DAMAGE TO RESIDUAL TUMORS TARGETED BY IONIZING AND NON-IONIZING RADIATION THERAPY

CROSS-REFERENCES TO RELATED APPLICATIONS

This application is a continuation-in-part of U.S. patent application Ser. No. 09/195,056, filed Nov. 18, 1998, which claims priority from provisional U.S. patent application Ser. No. 60/066,195, filed Nov. 19, 1997, now abandoned.

FIELD OF THE INVENTION

This invention relates to the treatment of tumors within an organism, and more specifically, to encapsulating, destroying and removing malignant tumors from an organism.

BACKGROUND OF THE INVENTION

Death from cancer most often occurs from metastases which become apparent years after the attempted curative surgery. Tragically, the very acts of biopsy and surgical excision disseminate tumor cells into the systemic circulation and into the regional lymphatics. Improvement in long term cancer survival is dependent on answering two questions: (1) How can we accurately diagnose cancer without shedding tumor cells? (2) How can we surgically remove tumors without shedding tumor cells, and without stimulating any residual tumor cells?

New possibilities for concentrating rare circulating tumor cells from the peripheral blood and possibilities for detection of rare tumor cells in marrow may allow adequate certainty to proceed with lumpectomy as biopsy, avoiding one tumor shedding exposure. If clinical presentation and diagnostic images are shown to be more than 90 percent predictive in defined circumstances, biopsy may also be bypassed with adequate informed consent. In cases where biopsy cannot be eliminated, strategies for minimizing tumor shedding should be evaluated. Broadly, both physical and chemical methods are possible.

Physical methods include blockade of lymphatics using injection of substances around the full three dimensional perimeter of the tumor (peritumoral injection) in order to clog or constrict the lumphatics. Peritumoral injection of the patient's fresh whole blood which has been freshly hemolyzed by addition of sterile water for injection is a physiologically attractive maneuver. Not only are the lymphatics obstructed by red cells, but tissue clotting mechanisms are activated and small veins may clot. Edema should further close off lumphatics and small veins. Local macrophage activation may result in destruction of some tumor cells.

Peritumoral blockade is probably not adequate by itself to eliminate tumor shedding in cases where the tumor itself is surgically entered, rather than only pierced by a biopsy needle. If we want to excise small tumors with minimal invasion, we need a truly robust way to contain and kill spilled tumor cells.

Primary and metastatic malignant tumors can be treated by a variety of methods, including surgical excision, chemotherapy and radiation therapy. A primary goal of all of these therapeutic methods is to remove and/or inactivate the tumor while causing as little collateral damage as possible to healthy tissues within the organism being treated.

Surgical excision of a tumor with a minimum of collateral damage to healthy tissues has been facilitated by advances in the arts of microsurgery, endoscopic surgery and real-time imaging. In particular, surgical techniques using surgical/imaging devices enable surgeons to precisely distinguish in real-time between tissues to be removed and tissues to be preserved intact within an organism. Unfortunately, it has been found that the very act of surgically excising a tumor from an organism, no matter how precise the surgical technique, can cause the tumor to metastasize, thus causing collateral damage to healthy tissues which may not become clinically apparent for months or years, but which will almost always progress to kill the patient.

Although advances in chemotherapy also promise to minimize collateral damage, researchers still seek a "magic bullet" which would effectively target only malignant tissues for destruction, without damaging healthy tissues.

In the meantime, it has been proposed to surround the tumor with a barrier which would protect surrounding healthy tissues from the damaging effects of locally injected chemotherapy. See, e.g., U.S. Pat. No. 5,458,597.

U.S. Pat. No. 5,458,597 deals with creation of a diffusion barrier of heat coagulated tissue proteins in order to restrict the outflow of locally injected chemotherapeutic agents from the thermally created tumor crater. Necrotic tissues and the coagulation capsule are left behind, where they are at substantial risk of becoming infected.

U.S. Pat. No. 5,472,441 teaches providing a radiofrequency induced tissue coagulation barrier around a tumor to contain locally injected chemotherapy. Only metastatic cancers with no prospect for cure would be suitable for such a palliative nonsurgical approach where the additional risk of shedding tumor cells by piercing the tumor is irrelevant because of the short lifespan of patients with metastatic disease. Failure to remove the killed tissues as taught in this patent places the patient at risk for infection.

Collateral damage to normal tissues adjacent to cancerous tumors also limits the effectiveness of radiation therapy. Radiation sensitizers have been sought to selectively increase damage to malignant tissues while sparing healthy tissues. Unfortunately, these radiation sensitizers can themselves be toxic to healthy tissues when injected at levels high enough to achieve their radiation enhancing effect, and/or might not persist in the area of the tumor for a time sufficient to enhance the effect of radiation on the tumor.

Thus, there is a still unsatisfied need for tumor therapies that are effective in removing and/or inactivating the tumor without causing significant collateral damage to healthy tissues, and without causing microscopic shedding of tumor cells which create diagnosable metastases months or years later.

All references cited herein are incorporated herein by reference in their entireties.

SUMMARY OF THE INVENTION

The instant invention addresses at least the foregoing deficiencies of the prior art by providing methods for conducting an operation on a living organism, said method comprising:

providing a channel around a tissue of said organism; and infusing into said channel an encapsulating composition to encapsulate said tissue in a capsule, wherein said capsule impedes materials encapsulated therein from migrating to other tissue outside said capsule.

Also provided are apparatuses for performing methods of the invention.

The invention also provides an improved method of radiation therapy comprising administering a radiation enhancing agent in or near a tissue to be treated. The radiation therapy method can conducted with or without encapsulation.

BRIEF DESCRIPTION OF THE DRAWINGS

The invention will be described in conjunction with the following drawings, which are not drawn to scale and in which like reference numerals designate like elements and wherein.

DETAILED DESCRIPTION OF PREFERRED EMBODIMENTS

The invention provides a method and an apparatus for creating a capsule which contains tissue to be treated, destroyed and/or removed, e.g., a tumor with adequate margins. The invention also provides a method and an apparatus for treating tissues with radiation-enhancing agents, particularly residual tissues remaining when total tumor removal is impossible.

Although much of the specification specifically pertains to the treatment of tumors, the invention is not limited thereto. The invention encompasses the isolation, treatment, destruction, and/or removal of other tissues as well.

In embodiments of the invention, a capsule surrounding a malignant or potentially malignant tumor can be provided, which prevents significant collateral damage by metastasis to tissues outside of the capsule, and optionally allows the tumor within the capsule to be treated more aggressively, yet safely, using minimal invasive surgical techniques, including ultrasonic tissue ablation, resectoscope, chemical digestion, and the like. Such aggressive treatment can include the provision of radiation enhancing agents to any unresectable tumor reside and/or to the tissues surrounding the capsule which are at risk of harboring viable tumor cells.

A preferred method of a tumor treating method of the invention comprises:

(a) Impeding fluid communication between the tumor and healthy tissues by reducing tumor vasculature and impeding fluid communication in tumor area lymphatics and veinules by injection-infiltration of materials causing sludging, clogging, constriction, compression, and/or coagulation.

(b) Forming a channel by severing all the clogged lymphatics and the compressed or coagulated venules and veins and arteries surrounding the tumor without cutting the tumor. Creation of a suitable 1–3 mm thick capsule space by spherical ablation of soft tissues with adequate tumor margins is preferably monitored by ultrasound.

(c) Filling the channel with an encapsulating composition. Injection and distribution of suitable capsule forming materials preferably using combinations of existing FDA approved materials.

(d) Forming the capsule. In situ capsule cross-linking with FDA approved iron and copper catalysts, driven by energy input from an intense visible light source.

(e) Evacuating the contents of the capsule. Evacuation of the tumor can be accomplished without risking damage to the capsule by using recessed rotating or reciprocating sharp blades with vacuum assisted entry of tumor into blade proximity. Existing minimally invasive biopsy technologies can be adapted.

(f) Internally sterilizing the evacuated capsule. Sterilization of the empty capsule interior can be achieved with absolute ethyl alcohol. Adjacent contaminated tissue from fissures or penetrations of the capsule wall would be simultaneously treated.

(g) Removing the capsule from the patient. Removal of the internally sterilized capsule wall can be accomplished in several alternative ways:
(i) Incision of the capsule wall and peeling of strips from within can be done using a simple winding tool.
(ii) Insertion of a sterile disposable sharp blade array can cut a fresh cavity along the outside of the capsule, freeing the capsule from external tissue attachment, allowing easy intact capsule extraction.
(iii) Vacuum applied to the trocar can collapse the capsule which can then be withdrawn be retraction of the attached trocar.
(iv) The distal end of the formed capsule can be tightly grasped with a suitable tool which is then withdrawn, everting the capsule within the trocar.

The fresh tissues exposed by removal of the capsule can be examined for residual tumor cells. If residual tumor cells are detected, a new capsule is created after obliterating the initial cavity with purse string sutures. Tumor bearing tissues are again evacuated and removed, as above. If complete surgical tumor excision is impossible, residual tumor is treated by local infiltration of radiation sensitizers and/or therapeutic deposition of radiation sensitizers and other tumor killing agents in a timed release artificial capsule.

Therapeutic infiltration of surrounding breast tissues with persistent radiation-chemotherapy sensitizers and potentiators and/or immunotherapeutics can be accomplished using a novel disposable diverging multineedle array through the created cavity without any additional skin penetration. Use of persistent colloidal iron and copper, iron dextran and copper dextran complexes, and iron and copper within a polymer matrix can be combined with oral, parenteral or timed release formulations of vitamin C and the amino acid Histidine. Precise tissue levels of immunotherapeutics such as the interleukins and interferons can be accomplished.

Formation of a therapeutic-aesthetic capsule will inhibit seroma formation and preserve breast volume and contour. Persistent immunoregulatory and apoptosis sensitization agents in a polymer matrix can fill the center of the timed disintegration therapeutic capsule, serving as a 12-month therapeutic reservoir.

Impeding Fluid Communication

Where local anatomy allows, the blood flow into and out of the cancerous tumor is blocked in a minimally invasive manner. Under Doppler ultrasound image guidance, the arteries supplying the tumor and the veins draining the tumor area are selectively coagulated outside the boundaries of the tumor by radio-frequency diathermal heat, preferably with a coaxial bipolar needle electrode. Use of Doppler ultrasound aids identification of blood flow in feeding arteries and draining veins and documents cessation of blood flow with successful diathermy heat coagulation. With successful devascularization, including vessels deep to the cancer, only the peritumoral lymphatic flow and flow in small veins remains to be blocked by chemical and or physical agents and processes, as discussed immediately below.

Flow in tumor area lymphatics and veinules is further decreased by injection-infiltration of materials causing sludging, clogging, constriction, compression and coagulation.

Peritumoral blockage of lymphatic flow and flow in small veins may be achieved by injection of appropriate substances such as combination of the patient's own whole blood, which has been freshly hemolyzed by addition of sterile water for injection, the patients own fresh plasma, vasoconstrictors, and substances which greatly increase local interstitial fluid viscosity prior to cutting and encapsulation. These measures can further reduce tumor cell shedding by sludging, clogging, constricting, compressing and coagulating peritumoral lymphatics and venules during the cutting process.

Red blood cells average 7 microns in diameter, which is relatively large for lymphatic channels. When sterile water for injection is added to blood, the red cells burst (hemolysis), creating abundant debris of smaller sizes more suited for clogging lymphatic channels.

Hyaluronans are valuable as agents to infiltrate around tumors prior to biopsy in order to reduce shedding of malignant cells into venules and lumphatics. Rheological properties of a 1% solution converting from a gel to a sol under pressure allow easy injection of a jelly-like material that subsequently swells by incorporation of adjacent tissue water. Thus, cells are immobilized both by increased viscosity as well as by increased local tissue pressure causing transient occlusion of lymphatics and venules. Rheological properties of converting from a gel to a sol under pressure, extreme hydrophilicity, and creation of dense interpenetrating polymer networks as well as tissue compatibility are very desirable properties of hyaluronans. See, e.g., Hoekstra, "Hyaluronan-Modified Surfaces for Medical Devices," Medical Device and Diagnostic Industry, pp. 48–58 (Feb. 1999), and the references cited therein.

Peritumoral tissue preparation, prior to cutting and encapsulation, can be accomplished by injecting:

(1) the patient's own fresh whole blood which has been freshly hemolyzed by addition of sterile water for injection.

(2) ferric lactate, which provokes an intense tissue reaction creating a rigid fibrous mass at the injection site. See Anghileri, Calcif. Tissue Int. 51:83–84, 1992.

(3) any sclerosing solution, such as are used to sclerose varicose veins, including adrenaline, norepinephrine, 95% ethyl alcohol, thrombin, ethanolamine oleate, ethanolamine oleate iopamidole, oleic acids, aethoxysclerol, polyethylene glycols, polydocanol, prolamine (Ethibloc), minocycline solution, doxycycline solution, tetracycline solution, erythromycin solution, silver nitrate, bleomycin, talc, quinacrine colloids, quinacrine solutions, quinacrine-ionic copper solution, phenol, phenol almond oil, sodium tetradecyl sulfate and OK432.

(4) tissue factor, fibrinogen or fibrin to induce clotting.

(5) collagen or gelatin to raise extracellular fluid viscosity.

(6) distilled water to induce edema, swelling tissues to pinch off venules and lumphatics.

(7) polyethylene glycol, including co-polymers and photo-initiating agent, to dramatically raise extracellular fluid viscosity and induce transient tissue solidification.

Mechanisms of action include pharmacologic vasoconstrictions, physical tamponade, chemical sclerosis, tissue dehydration, edema and thrombogenesis.

Forming a Channel

One or more cutting devices (e.g., blades, needle blades, lasers, wires, cords, torches, particle beams, etc.) which do not cut the tumor, sever all the clogged lymphatics and the compressed or coagulated venules and veins and arteries surrounding a tumor. The artificial capsule is created by providing (e.g., forming, cutting, etc.) a channel between the tumor and the surrounding healthy tissue.

In a preferred embodiment, a channel can be provided between the tumor-bearing tissue and surrounding healthy tissue by inserting at least one, and preferably an array, of shape memory metallic hollow side cutting blades or needles into the periphery of a tumor under real-time ultrasound, MRI, isotopic, x-ray guidance or combinations thereof. Preferably, the array comprises a plurality of deployable hollow radio-frequency or microwave antenna or laser or ultrasound energy activated needle blade elements. The array is expanded using cutting radio-frequency or microwave or laser or ultrasound power and rotating 1 to 20 energy depositing elements to cut and define a common onion-shaped, spherical or cylindrical surface, thus isolating a core of tumor-bearing tissue from adjacent healthy tissues, hopefully without tumor at the margins. In a preferred embodiment, every other (i.e., alternating) radio-frequency peripheral hollow element can be active or ground, producing a circumferential rather than a radial radio-frequency energy field. This blade design eliminates the need to pierce the actual cancer until after capsule formation, minimizing the chance to dislodge cells. FIGS. 1A, 1B, 1C and 2 show needle blades 10 which create such a channel when deployed and manipulated through a trocar 12. In order to minimize the amount of healthy tissue placed (e.g., trapped) within the capsule, it is preferable to use advanced imaging and/or marking means to precisely distinguish between malignant and healthy tissues when creating the channel surrounding the tumor.

The individual blades 10 may be of reshaped spring steel, and may also be fabricated using a metal with shape memory or a bimetallic spring material, wherein shape alters as a function of temperature to cause bending in response to applied energy activation.

Multiple rotations of the blades 10 are performed during slow advancement of the device under diathermy, microwave, laser, ultrasound cutting power. Real-time imaging ultrasound inspection as the process is being performed allows appropriate enlargement of the cut volume of tissue to include any detectable irregularities of tumor shape appearing too near the cut margin. Real-time ultrasound imaging inspection as the process is being performed allows assessment of the completeness of isolation of tumor from surrounding tissues, allowing timely appropriate remedial actions, prior to installation of capsule forming materials. A suitable 3 mm thick capsule space can be created by spherical ablation of soft tissues with adequate margins by ultrasound.

A 5 mm skin incision allows introduction of a sharp trocar which is advanced to within 7 to 10 mm of the nearest tumor margin and centered. Multiple extendable sharp hollow blade elements are deployed to surround the tumor with a 7 to 10 mm margin from tumor edges. These sharp blades may be ultrasonically driven and are slowly rotated in the sharp direction. The preferred blade tapers from a knife edge to a 1.5 mm trailing edge which has multiple orifices to serve as a fluid suction and deposition device. The larger the number of blades, the less rotation is required to cut a complete isolating cavity. Absolute ethyl alcohol can be expelled from odd blades while even blades suction blood and alcohol diluted with tissue fluids. Some tissue shrinkage occurs from absolute ethyl alcohol dehydration. If tumor cells are accidentally transected, alcohol sterilization of shed cells is rapid.

If desired cutting, coagulation and tissue dessication can be achieved using bipolar radiofrequency, where odd blades are energized and even blades are grounded. In the radiofrequency approach, it may be preferable to irrigate with only hypertonic saline flowing from the odd blades instead of absolute ethyl alcohol to avoid heating a potentially flammable fluid while even blades suction blood and hypertonic saline diluted with tissue fluids. Moderate heating of absolute ethyl alcohol passing through the activated radiofrequency blades will be proven safe by suitable experiments.

Filling the Channel

The channel is filled with an encapsulating composition to form a capsule wall. In embodiments, the encapsulating composition is extruded into the channel through the hollow blades 10.

Unlike the barrier taught in U.S. Pat. No. 5,458,597, the capsule of the invention does not consist primarily of rigid, brittle heat denatured local tissue components, but rather consists predominantly of injected materials which mix with the patient's own wound blood to form a tough, flexible capsule. The capsule is preferably created by chemical reactions between naturally-occurring components of the patient's own blood, such as plasminogen and fibrinogen, and components of a capsule-forming composition comprising substances (e.g., collagen) that combine with the patient's body chemistry to create a tough, flexible capsule. Alternatively, the capsule may be created with a capsule-forming composition comprising a barrier-forming or film-forming substance, which forms the capsule without chemically reacting with naturally-occurring molecules. In any event, the encapsulating composition preferably transforms from liquid to (a preferably elastic) solid form after being injected into the channel. Ultraviolet chemical curing lights, such as are commonly used for curing dental materials, may be used to initiate photopolymerization of capsule forming materials which have been doped with suitable photoinitiator compounds.

The capsule can be formed by injection and distribution of existing FDA approved materials. For example, silk-elastin engineered protein polymers developed by Protein Polymer Technologies, San Diego, Calif., may be useful either singly, or as copolymer ingredients. Use of these or other existing FDA authorized protein polymers may greatly speed time to market. United States Surgical clearly has a significant technology base in approved suture materials which should be adaptable to capsule formation in vivo. Bard's Contigen product appears to be another rapidly approvable capsule material.

Rheological properties of a 1% hyaluronic acid solution converting from a gel to a sol under pressure allow easy injection of a jelly-like material that mixes well with other capsule constituents and subsequently swells by incorporation of adjacent tissue water. Hyaluronic acid is a member of the glycosaminoglycans (also known as mucopolysaccharides), which may have an important role as additional constituents of the formed in place capsule. Covalent cross-links of a mucopolysaccharide (6% to 15% by weight) mixed with collagen at pH 3 to 6 at 37° C. forms an average molecular weight between cross-links value of 5,000 to 10,000. Thus, the collagen fibers reinforce the mucopolysaccharide matrix, leading to outstanding mechanical properties. The preferred upper limit of beneficial addition of chondroitin 6-sulfate is 28%, and of hyaluronic acid 25%. Addition of 10% by weight of chrondroitin 6-sulfate to collagen increases fracture work from 1900 to 7100 psi-%. See U.S. Pat. Nos. 4,280,954, 5,520,916, and 5,807,581.

Covalent cross-linking of non-toxic biocompatable polymers has been accomplished in living animals with continuous films of good mechanical strength. See, e.g., West et al., "Comparison of covalently and physically cross-linked polyethylene glycol-based hydrogels for the prevention of postoperative adhesions in a rat model." Biomaterials 16:1153–1156, 1995. West et al. describe using the photoinitiator 2,2-dimethoxy-2-phenyl acetophenone at 900 parts per million and photopolymerizing the polyethylene glycol inside the living animal by 20 second exposure to 365 nanometer ultraviolet light, at 10 milliwatts/cm$^2$, to produce a strong, resilient, covalently cross-linked, continuous barrier that was intact for over 4 days.

Potential capsule forming materials include ingredients of all synthetic and naturally occurring resorbable suture materials and coatings, including Proline and Vicryl, silk-elastin engineered protein polymers, collagen, polymerized amino acids, polymerized peptides, polyethylene glycol polymers and co-polymers, hyaluronans, glycosaminoglycans, alginic acid, glucuronic acid, N-acetylglucosamine synthetic compounds and esters, chrondroitin sulfates, keratin sulfate, dermatin sulfate, urethanes, glycerin, gelatin, advanced glycation products, reactants of the foregoing with alcohols and aldehydes, as well as dehydrothermal cross-linked reactants of the foregoing. Coprecipitates of collagen, a glycosaminoglycan, a polysaccharide gel, cellulose, semi-synthetic polymers, and synthetic polymers are also feasible. Polysaccharide gels can be selected from the group consisting of chitosan, chitin, pectin, pectic acid, agar, agarose, xanthan gum, gellan, alginic acid, an alginate, polymannan, a starch, and a polyglycan. Synthetic polymers can be selected from the group consisting of polyglycolic acid, polylactic acid, a copolymer of polylactic acid and polyglycolic acid, a polydioxane, a polyphosphazene, a polyurethane resin, and a polysulfone resin.

Ethyl or benzyl esters of hyaluronic acid dissolved in DMSO can be reacted with polyethylene glycols or ethyl alcohol within the wound cavity.

Dehydrothermal cross-linking of the capsule ingredients can be facilitates by injections of absolute ethyl alcohol into the tumor, which dehydrates the tumor and thus at least the inner surface of the capsule. Such dehydration of tissues within the capsule can be repeated with strongly hypertonic salt solutions alternating with repeated injections of absolute ethyl alcohol. Then the tumor volume can be directly heated by any means. The simplest means may be insertion of bipolar radiofrequency needles to coagulate the tumor. The combination of dehydration and heat significantly increases cross-linkage within the capsule materials, producing a much tougher penetration resistant material. Subsequent removal of largely necrotic tissues from within the capsule can then proceed by any means.

Silk-elastin engineered protein polymers developed by Protein Polymer Technologies, San Diego, Calif. may be useful either singly, or as copolymer ingredients. Use of these or other existing FDA authorized protein polymers may greatly speed time to market.

Additional important work on engineering the desired strength co-polymerization is disclosed in Suggs et al., "Preparation and characterization of poly(propylene fumarate-co-ethylene glycol) hydrogels." Journal of Biomaterials Science Polymer Edn. 9: 653–666, 1998.

The encapsulating composition is adapted to provide a capsule which prevents migration of tumor cells into regional lymphatics and into veins during surgical manipulation and during surgical removal of the abnormal tissue. Preferably, the encapsulating composition is adapted to provide a capsule which contains the chemical and physical tumor sterilization-destruction-digestion-fragmentation process, protecting adjacent tissues from chemical and physical damage attendant to tumor removal.

The encapsulating composition is preferably designed in view of the desired curing method. Curing (i.e., solidifying) can be a function of time, temperature and/or other naturally prevailing or artificially provoked conditions. Thus, for example, the composition can comprise: components that react with each other to polymerize within a predictable amount of time after mixing; components that melt at a temperature above body temperature (i.e., >37° C.), are applied as a hot melt and cool to form a solid capsule at body temperature; components that react with naturally prevailing molecules in the patient to form solids or semi-solids; and/or components that polymerize in response to radiation (e.g., ultraviolet radiation applied after injection into the channel). In situ capsule cross-linking with iron and copper catalysts, can be driven by energy input from an intense light source.

Iron and copper catalysis of polymerization can involve existing approved injectable iron dextran and copper sulfate formulations, added to the polymer slurry as it is stirred within the capsule space by continuing slow rotation of the blades, which are withdrawn just prior to light activation.

Use of approved FDA light sources, such as those currently applied to dental restorative materials, can cut the time to market. Fiberoptic delivery of visible light from consumer slide projection bulbs can also create an inexpensive curing energy source, which could be quickly approved.

Additional dehydration cross-linking of the capsule can be accomplished by tumor dehydration/shrinkage/sterilization with alternating infiltrations of absolute ethyl alcohol and hypertonic salt solutions. Other chemical and physical dehydration means can be exposed. Staying with approved products decreases time to market.

Tumor heating and coagulation by inserted bipolar radiofrequency electrodes will also produce additional thermal cross-linking of the capsule. Optional patentable inductive heating of metal colloids and ions dispersed in the capsule materials (and optionally also within the tumor) would produce additional thermal polymerization of the capsule.

If an adequately tough capsule can be formed by light driven metal catalyzed cross-linking alone, dehydrothermal steps may be redundant.

Suitable encapsulating compositions are formulated to provide capsules with properties that enhance or are complementary to the particular activities being performed within the capsule. Thus, for example, a biocompatible polymer that is resistant to the mechanical and/or chemical means for destroying the tumor is preferably selected. The encapsulating composition can comprise a combination of materials selected for their various advantageous properties. Materials potentially useful in artificial capsule formation can be found in the book *Surgical Adhesives and Sealants Current Technology and Application,* edited by David Sierra et al. (Technomic Publishing 1996, Library of Congress #95-61620).

The encapsulating composition is adapted to provide a capsule which prevents migration of tumor cells into regional lymphatics and into veins during surgical manipulation and during surgical removal of the abnormal tissue. Preferably, the encapsulating composition is adapted to provide a capsule which contains the chemical and physical tumor sterilization-destruction-digestion-fragmentation process, protecting adjacent tissues from chemical and physical damage attendant to tumor removal.

The encapsulating composition is preferably physiologically compatible, although in certain circumstances physiological incompatibility is tolerable. For example, localized toxicity is acceptable when the method is employed as a palliative measure in terminal patients.

It is particularly advantageous to include a marking agent (e.g., an imaging ultrasound, x-ray, magnetic resonance or combined marking agent) in the encapsulating composition so that the artificial capsule can be readily evaluated by imaging techniques, and if the capsule is to be removed at the end of the procedure, any remnants thereof remaining in the patient can be readily identified.

If the capsule is to be removed after its evacuation, it is advantageous to provide an elastic capsule which does not adhere to body tissues.

It should be noted that the capsule typically extends to and bonds with the perimeter of the introducing needle or trocar, forming a sealed system, sealed to the outer skin, open to the outside of the body. The length of the capsule to trocar seal may be increased by advancing the trocar further into the tumor while partly retracting blades 10 after the encapsulating composition has been freely applied within the channel.

The capsule provided by the methods and devices of the invention has at least the following beneficial effects. First, the capsule prevents materials inside the capsule from contacting and damaging tissues outside the capsule. Second, the capsule can enhance the anti-tumor effectiveness of the therapy by maintaining the focus of the therapy within a confined area surrounding the tumor.

Evacuating the Capsule

After the capsule has fully formed and optionally passed inspection of its integrity and scope (e.g., via real-time ultrasound, MRI, x-ray or fluoroscopy), any combination of chemical, physical and/or mechanical means of tissue destruction are employed to destroy the contents of the capsule. Prior to beginning tissue liquefaction or mechanical tissue removal, it is desirable to chemically kill and disrupt and partially digest most tumor cells with: desiccants, such as absolute ethyl alcohol; cell bursting agents, such as distilled water; free-radical catalyst, such as iron and copper ions; free-radical chemical reaction initiators, such as hydrogen peroxide and hypochlorite bleach solution; and/or halogenators such as iodine tincture. Enzymes, such as colligenase, chondroitin sulfate, and DNAase, as well as proteolytic enzymes, such as trypsin, which are physiologically secreted by the pancreas, may be used to digest tissues. Papain and other common biochemical enzymes may also be used. Use of radio-frequency cutting and coagulation as well as adaptation of the common resectoscope normally used for transurethral resection of the prostate are also appropriate. Ultrasound, laser, microwave or radio-frequency energy can be deposited in the tissue to be destroyed using tumor penetrating probes or through skin or nearby tissues such as the vagina, bowel wall, oral cavity or other energy transmission site external to the capsule.

Ultrasound energy can be very effective in tumor destruction-digestion-fragmentation. Ultrasound has been used in cataract emulsification and in brain tumor debulking. Ultrasound energy induces local hyperthermia which is beneficial in tumor killing and lysis. Local hyperthermia significantly increases the rate of all chemical reactions.

Mechanical means for tissue removal analogous to those employed in prostate surgery, including resectoscope, electrovaporization, microwave needle ablation and thermotherapy, high intensity focused ultrasound, and various forms of laser ablation, are all applicable to minimal access tumor therapy of artificially encapsulated tumors. See also "Surgical and Minimally Invasive Therapies for BPH," 3(1) Harvard Men's Health Watch (August 1998), which describes many techniques for removing prostate tissue from within the natural capsule.

Physical means of destroying the tumor within the previously created protective capsule, such as high power diathermy coagulation, diathermy dehydration and diathermy cutting, are readily available using the cutting needle array that created the capsule wall space. Additional physical processes, such as, e.g., focal heating and focal freezing, are also suitable.

The invention enables complete removal of large tumors from anywhere in an organism through a small, minimal access puncture, by liquefaction and removal of the contents of the artificial capsule. Liquefaction is preferably accomplished by physical means, such as comminuting the tissue with a moving (e.g., rotating, reciprocating, etc.) slicing means (e.g., a spinning cord or blade) to which the capsule walls are resistant, and/or chemical means. Most preferably, the contents of the artificial capsule are liquefied using ultrasonic energy, preferably having a wavelength of about 20 to about 40 kilohertz, transmitted through a titanium wand incorporating irrigation and suction functions. Use of radio-frequency cutting and coagulation as well as adaptation of the common resectoscope normally used for transurethral resection of the prostate is also appropriate.

As is well known, the overwhelming majority of each cell is made up of water, along with lipids, and proteins including collagen. Thus, liquefaction of tissues is an attractive option for tumor removal. To liquefy tissues, one must burst lipid cell membranes. Tumor tissues may be particularly sensitive to destruction by high power ultrasound, even in the absence of pretreatment with hypotonic solutions, because tumor cells generally exhibit higher intracellular pressures than are found in normal cells. Pretreatment with absolute ethyl alcohol sucks water out of cells and injures cell membranes. Sterile distilled water subsequently administered rushes into the dehydrated cells, bursting them.

Figure 1A:
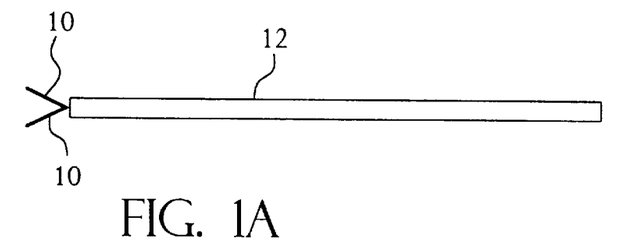
FIG. 1A is a side view of one embodiment of the apparatus of this invention shown being deployed through a trocar for carrying out a method of this invention, with the apparatus comprising a pair of extendable hollow blades shown in their retracted position.
Figure 1B:
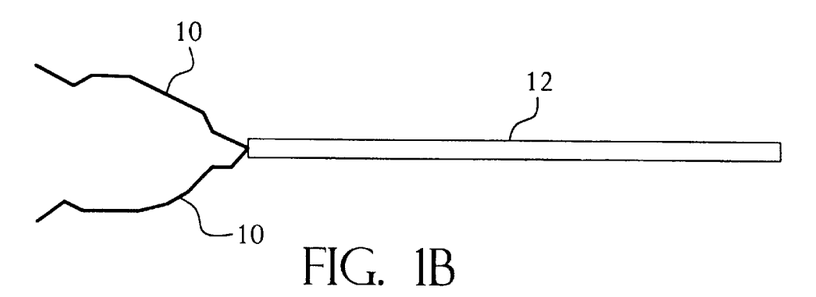
FIG. 1B is a side view, similar to FIG. 1A, but showing the apparatus at later state of deployment wherein the blades are partially extended.
Figure 1C:
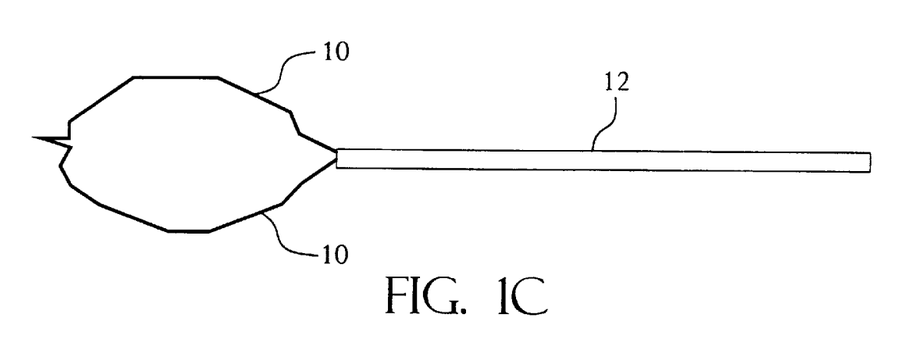
FIG. 1C is a side view, similar to FIGS. 1A and 1B, but showing the apparatus at later state of deployment wherein the blades are fully extended.
Figure 2:
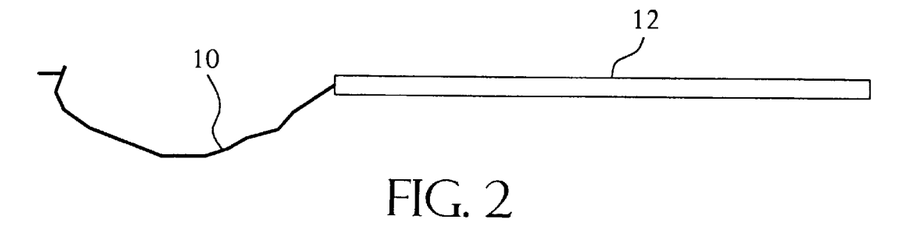
FIG. 2 is a side view, similar to FIG. 1A, but showing of an alternative embodiment of the apparatus of this invention, namely, a single hollow blade embodiment shown with its blade in the fully extended state.
Figure 3:
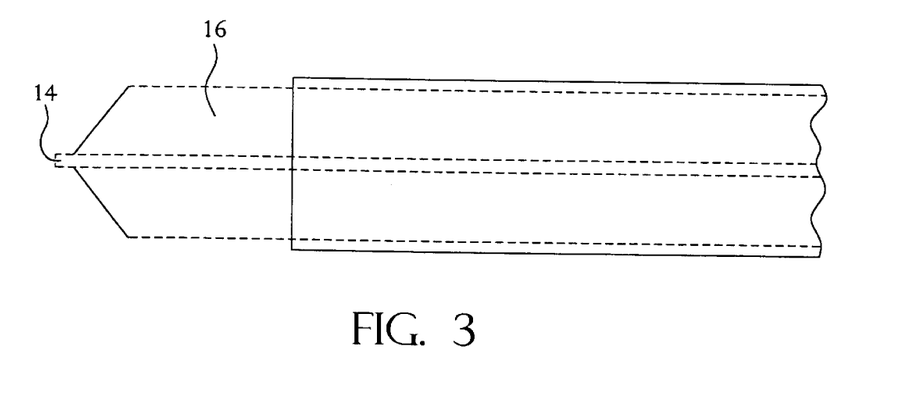
FIG. 3 is a side view of the distal end of an ultrasonic tissue destruction and removal probe constructed in accordance with this invention and useful for performing a method of this invention.
Figure 4:
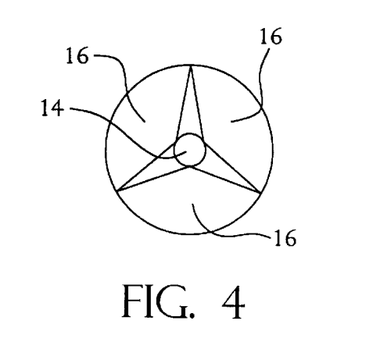
FIG. 4 is a front (distal) end view of the probe of FIG. 3.
Figure 5:
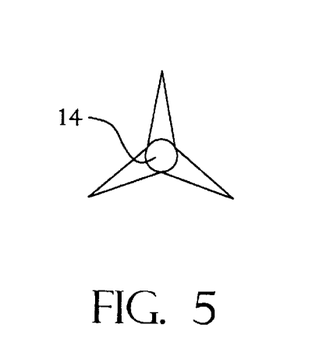
FIG. 5 is a view similar to FIG. 4, but showing an alternative embodiment of a tissue destruction and removal probe of the invention.

Membrane destruction may be done with physical energy, such as 20 to 40 kilohertz frequency high energy ultrasound, or by chemical means, or preferably by a combination of chemical pretreatment, metallic colloid treatment, augmented by subsequent 20 to 40 kilohertz frequency high energy ultrasound. High power 20 to 40 kilohertz ultrasound bursts cell membranes especially well if prior exposure to a hypotonic solution has caused cells to swell. Such high energy ultrasound also focally heats tissues, and vastly increases chemical and catalytic reactivity of metallic powders or colloids which may have been previously deposited in said tissues. Conventional 20 to 40 kilohertz frequency high power ultrasound titanium probes which have heretofore been used for fat reduction surgery can be adapted for tumor removal. This technique produces micromechanical effects, cavitation effects, and thermal effects, as documented in Zocchi, "Ultrasonic Liposculpting," Aesth. Plast. Surg. 16:287–298, 1992. Zocchi advocates infiltration of large volumes of physiologic salt solution 50% diluted with distilled water to render the cells vulnerable to ultrasound energy induced cell bursting. Zocchi also uses the enzyme chondroitin sulfate. As shown in FIGS. 3 and 4, improvements over Zocchi's design (which more closely resembles the alternative embodiment of the invention depicted in FIG. 5) include a central passage 14 for irrigant and a coaxial suction cannula 16 adjustably positioned around a multi-edge, preferably titanium, ultrasound energy transmitting probe. Further improvements over Zocchi include use of absolute ethyl alcohol, followed by distilled water, as well as free-radical reaction catalysts, such as iron and copper ions, free-radical chemical reaction initiators, such as hydrogen peroxide and hypochlorite bleach solution, and halogenators, such as iodine tincture. Powders and colloids of iron and copper may provide significant chemical catalytic free-radical mediated tissue destruction by chemical and physical increase in reactive surface as documented by Suslick et al., "On the origin of sonoluminescence and sonochemistry," Ultrasonics 28(5) 280–290, September 1990.

Alternatively, a rigid tube may be inserted which has rows of orifices along its circumference through which cords, wires or blades are radially deployed into the adjacent tissue. Multiple rows of radical elements are deployed into the encapsulated tissues in this manner to transmit ultrasound, microwave, diathermy or other energy forms into the tissue. The degree of destructive energy can be modulated to achieve the desired degree of cell killing and/or liquefaction. Similarly, a multiplicity of fine wires may be deployed, which are hollow at their core, thereby allowing hypodermic injection of selected chemical or biochemical substances throughout the volume of the tumor to selectively increase the tissue destruction either by more efficient coupling with the energy field being deposited, or in order to propagate chemical reactions that are induced by the deposition of energy. Specifically, free-radical reactions can be supported by the presence in tissue of elemental iron or copper, especially of selected valences.

Alternatively, the tumor can be macerated within the artificial capsule with a grinder suction probe modeled on "rotorooters" used to remove atherosclerotic plaque, a side cutting tissue auger with attached suction probe. Mechanical tumor removal can also proceed by more conventional mechanical tumor removal by resectoscope, side-cutting or end-cutting minimally invasive surgical instruments such as the ABBY™ of BIOPSYS™ systems, vacuum assisted auger or "rotorooter" tissue extraction, or various means of mechanical tissue maceration. The capsule contents can also be removed by endoscopic or direct visually guided dissection.

Wires, cords and/or fibers can be introduced and rapidly rotated like a WEED WACKER™ gardening device. Such rotatable elements can effectively mince tissue, allowing the suction removal of tissues that have been destroyed. In order to minimize the transmigration of viable tumor cells into the bloodstream or into the lymphatics, encysting and appropriate biochemical treatment of the tumor prior to mechanical mincing may be valuable. In one embodiment, thin metallic blades are advanced to extend beyond the diameter of the trocar in order to engage tissue. The needle shaft in its entirety, or just the portion of the needle shaft that has the blade elements projecting therefrom, is then rapidly rotated coaxially with the needle shaft. Thus, an approximately cylindrical volume of tissue is minced in situ. Application of irrigation solution and application of suction facilitates the removal of the debris, leaving only healthy tissues behind.

There are many ways in which tissues can be mechanically minced or destroyed by movement of elements designed to whip, shred, or mince tissues. In general, a roughly spherical volume of tissue destruction can be readily achieved. Similarly, roughly cylindrical volumes of tissue destruction seem readily achievable. Additionally, more specialized volumes and shapes can be achieved by modification or repositioning of the tissue destructive elements emanating from the placement needles.

Micromotors which can individually drive the tissue destructive elements so that the individual elements can rotate as well as be moved by the movement of the shaft of the needle. That is, the elements can be rotated about their own axis or whipped about similar to a WEED WACKER™ while at the same time the shaft of the needle upon which they are mounted is also rotating on its own axis. In such a way, more extensive tissue destruction is rapidly achieved. One advantage of mincing, liquefying and removing the cancerous tumor is to assure that complete tissue destruction has, in fact, occurred. If the tumor is simply destroyed in its location and allowed to remain, a palpable lump persists. If the tumor, having been killed, is then minced, liquefied and withdrawn from the body, it is possible that healing may occur without production of a palpable area of scar tissue. Thus, assurance that the tumor is not regrowing would be provided.

Physical means of tissue dehydration and dicing, such as heat and cutting created by diathermy, can be useful. In the preferred diathermy embodiment, every other alternating diathermy peripheral element is either active or ground, producing a circumferential rather than a radial diathermy energy field. This design eliminates a need to pierce the actual cancer, minimizing the chance to dislodge cells. The diathermy coagulation power can preferably be applied using the same alternating active or ground elements. For this use, cutting power is applied to the antenna array as it is pulled back from the created capsule wall, to a position about ⅔ the capsule diameter. To maintain clearance from the capsule wall closest to the surface, the trocar may be pushed further forward under ultrasound control. Much higher coagulation diathermy power is then applied under real-time ultrasound visualization to heat, kill, and shrink the tumor bearing tissues within the capsule, without injury to the capsule wall or to tissues beyond the capsule wall.

Alternatively, after capsule formation, a bipolar diathermy system with a central needle serving as ground electrode pulse 1 to 20 wire antennas radiating to surround the central ground can be inserted into the encapsulated tumor to define a spherical or cylindrical diathermy field. The configuration may resemble antennas deployed on space satellites.

Many physical, chemical, and mechanical processes can dramatically reduce solid volume while killing cells, allowing removal of large volumes of tissue through minimal access surgery. It will be apparent to those having skill in the art that this and other features of the invention make the invention particularly advantageous for treating breast, brain and lung tumors.

Internally Sterilizing the Evacuated Capsule

After removal of the capsule's contents, it is preferred to sterilize the remaining inside capsule wall and instrument track.

Chemical tumor sterilization and destruction-digestion-fragmentation means include: dehydration by absolute ethyl alcohol, optionally followed by povodine-iodine, and then by osmotic cell bursting using distilled water or other hypotonic solutions; enzymatic degradation, including digestion by collaginase and/or pappain; acid and/or base degradation; applying sodium hypochlorite solutions, applying hypertonic salt solutions; applying local hyperthermia, and applying tincture of iodine. Final sterilization of the tumor bed and instrument track can be achieved by providing chemical sterilization agents within the capsule's interior. Suitable chemical sterilization agents include free-radical catalysts, such as iron and copper ions, initiators, such as hydrogen peroxide and hypochlorite bleach solution, halogenators, such as iodine tincture, desiccants, such as absolute ethyl alcohol, and cell bursting agents, such as distilled water causing osmotic rupture. Physical heat from diathermy or cell membrane bursting from high power ultrasound is useful for final sterilization of the capsule interior, capsule exterior, and instrument track.

Removing the Capsule

Removal of the internally sterilized capsule wall is preferably accomplished in several alternative ways:

(i) Incision of the wall and peeling of strips from within can be done using a winding tool.

(ii) Insertion of a sterile disposable sharp blade array can cut a fresh cavity along the outside of the capsule, freeing the capsule from external tissue attachment, allowing easy intact capsule extraction. Ultrasound and/or radiofrequency power can be applied to the blades as needed.

(iii) Vacuum applied to the trocar can collapse the capsule which can then be withdrawn be retraction of the attached trocar.

(iv) The distal end of the formed capsule can be tightly grasped with a suitable tool which is then withdrawn, everting the capsule within the trocar.

Thus, the sterilized capsule wall is safely removed by peeling with a suitable tool, by resectoscope (e.g., as commonly used in prostate surgery), by endoscopic or direct surgical dissection, or by side-cutting or end-cutting minimally invasive surgical instruments, such as the ABBY™ or BIOPSYS™ systems. Capsule wall removal technique can mimic opening a sardine can by peeling the capsule membrane onto a key like tool. Removal of the capsule wall eliminates a palpable residue that could mask local tumor recurrence. Final treatment of the cavity after removal of the capsule wall by installation of residual action locoregional tumor bed and lymphatic treatment agents can be performed.

If the capsule wall is to be left in place, suitable sustained-release materials can be incorporated into the created capsule wall. Suitable sustained-release materials include, e.g.: chemotherapeutic agents; sterilization agents; biological response modifying agents, such as histamine, cytokines, and anti-growth factor blockers; and radiation-enhancing agents, such as ferric lactate.

Local timed release of therapeutic agents over weeks to months can be achieved by incorporating biologically active proteins, peptides, amino acids, molecular recognition units, biological receptor agonists and antagonists as well as drugs into the actual molecules being formed into resorbable capsules. Resorption of the capsule materials may release various colloidal or microencapsulated therapeutic agents designed for further timed disintegration. Some of said colloidal or microencapsulated therapeutic agents are designed to interact with local and regional lymph nodes and associated immunologically important cells. Biological, drugs, pro-drugs, as well as metal ions and diverse colloids may be incorporated.

Malignant diseases can be favorably influenced by release of physiological agonists for desired functions as well as release of antagonists against harmful processes. Modulation of the function of lymphatics in malignant diseases may increase cellular and humoral immunity to tumor cells as well as minimize infections and speed healing. Natural killer cells can be multiplied and activated. Immunization with purified antigens, immunodominant peptides, DNA, and recombinant viruses in combination with interleukins and other cytokine activators as well as tumor necrosis factor-alpha and CD80 and CD86 co-stimulatory molecules, can be accomplished using this locally persistent therapeutic capsule approach. See, e.g., the entire March/April 1999 issue of CA: A Cancer Journal for Clinicians, Volume 49, No. 2, entitled "Immunotherapy for Cancer: Current Concepts," and all the individual references contained therein.

Lymphatics that harbor tumor cells may be targeted with biological, chemical, and physical agents to increase tumor cell destruction. Histamine, bradykinin, vasopressin, interleukins, cytokines and amino acids such as histidine can readily be added to capsule materials as solutions and/or as colloids.

Therapeutic timed release substances for malignant disease include hormone effect blockers and hormone receptor blockers, promoting factors for cell differentiation, apoptosis, non-apoptotic cell death, DNA strand breakage factors, substances for converting single strand DNA breaks into far more lethal double strand breaks, free radical promoting factors, radioactive isotopes including release of radioactive colloids as lymphatic treatment, elements for neutron activation into radioactive isotopes, metal ions including iron and copper, histidine, ascorbate, peptides, radiation sensitizing agents, and chemotherapy agents as well as, antibodies, pro-drugs, anti-sense DNA, somatostatin, interferon beta, differentiation factors, peptide and protein products of tumor suppressor genes, as well as tumor suppressor genes themselves.

Suitable agents to control to growth of cancerous tumors or to minimize cancer cell shedding include:

1. Biologicals, such as:
   a. Angiogenesis inhibitors; blockers of angiogenesis promoters; and blockers of inactivation of angiogenesis inhibitors.
   b. Differentiaton promoters; blockers of inactivation of differentiation promoters; and blockers of dedifferentiation.
   c. Tumor necrosis factors; blockers of inactivators of tumor necrosis factors; and activators of tumor necrosis factor gene expression.
   d. Growth inhibitors; blockers of inactivation of growth inhibitors; and blockers of growth promoters.
   e. Antibodies, fragments, and molecular recognition units; and blockers of inactivation of antibodies, fragments, and molecular recognition units;
   f. Blockers of antibodies, fragments, and molecular recognition units.
   g. Products of tumor suppressor genes; and blockers of inactivation of products of tumor suppressor genes.
   h. Tumor suppressor genes; reactivators of tumor suppressor gene expression; and blockers of inactivation of tumor suppressor genes.
   i. Blockers of oncogene expression.
   j. Inactivators of oncogene products.
   k. Histamine, bradykinin, and vasoactive intestinal peptide.
   l. Somatostatin.
   m. Histidine.
   n. Vasopressin and oxytocin.
   o. Interferons.
   p. Chemotactic and promoting factors for natural killer cells.
   q. Estrogen receptor blockers and post receptor effect blockers.
   r. Tamoxifen and related compounds.
   s. Testosterone receptor blockers and post receptor effect blockers.
   t. Lupron and related compounds.
2. Drugs, chemicals, and metals, such as: antineoplastic drugs and pro-drugs, blockers of inactivators of antineoplastic drugs, radiation sensitizers, chemotherapy sensitizers, DNA single strand to double strand break completers, blockers of inactivators of DNA double strand break completers, catalytic metals including copper and iron, viscosity altering agents, and edema forming agents.

The capsule interior can be examined by standard optical or video endoscopic or laparoscopic or other minimal access surgical tools.

Exposed fresh tissues are examined for residual tumor cells. In order to document the tumor-free status of normal tissue margins, pathology touch preparations or tumor bed cell washings for automated cell sorting are obtained from the freshly exposed tissue walls after the capsule has been removed from the patient. If margins are tumor positive, the procedure is repeated to encapsulate a larger volume of tissue, or a side lobe of tissue. In embodiments, an enlarged capsule is formed around a temporary support structure provided by a balloon expanded within the void created by evacuation of the contents of the original capsule. Alternatively, the initial void can be closed with internal pursestring sutures, allowing reexcision with standard size channel cutting instruments.

Therapeutic Capsule and Persistent Tissue
Deposition of Angiogenesis Blockers

Angiogenesis promoters include naturally occurring molecules such as Endostatin (a fragment of type 18 collagen), Angiostatin (a fragment of plasminogen), Vasostatin (a fragment of calreticulin), Thrombospondin (platlet factor 4), troponin-1, and various coagulation regulator fragments. Angiogenesis blockers are preferably incorporated into the artificial capsule. The drugs Fumigillin (TNP-470) and Thalidomide have potent antiangiogenesis effects. Interferon beta physiologically opposes proangiogenic factors, leading indirectly to antiangiogenesis. Interferon beta cross-regulates collaginase, thus interferon beta physiologically opposes collaginase, preventing tumor expansion into surrounding tissues. Interferon beta also downregulates basic fibroblast growth factor, limiting tumor growth. Continuous availability of low levels of interferon beta (5,000 to 10,000 units) in a mouse model blocks angiogenesis; very importantly, higher interferon levels are ineffective. Angiogenesis can be blocked by antibodies against vascular endothelial growth factor, antibodies against basic fibroblast growth factor, as well as antibodies against any proangiogenic factor. Even common drugs such as angiotensin converting enzyme inhibitors can decrease growth of both tumor cells and vascular cells.

Some of the many materials suitable for forming capsules within the body and releasing locally active therapeutic agents over weeks to months include: silk-elastin engineered proteins, collagens, hyaluronans, proline, vicryl, synthetic suture materials, polymerized amino acids, glycerin, gelatin, synthetic polymers, polyethylene glycol, polyurethane, polyHEMA, polyurethanes, polyesters, polyolefin, natural and synthetic co-polymers and proteins.

Tissue Infiltration with Persistent Therapeutic Agents

The same design of disposable multi-cutter hollow array which can be used to cut the capsule cavity can be used before creation of the capsule or after removal of the capsule to diffusely infiltrate a persistent radiation sensitizer or a therapeutic isotope or other therapeutic agent throughout the affected tissue (e.g., breast) by serially inserting said device: first through the tissues at the far end of the cavity to infiltrate distal tissues, then with the prongs spread maximally through the tissues radial to the middle of the cavity, then through the subcutaneous tissues surrounding the tissue entrance proximal to the cavity. Therapeutic infiltration of surrounding breast tissues with persistent persistent radiation-chemotherapy sensitizers and potentiators and/or immunotherapeutics using a novel disposable diverging multineedle array can be accomplished through the created cavity without any additional skin penetration. By thus utilizing the entry channel and encapsulation space a very substantial volume of breast tissue can be treated without additional skin entrance wounds.

Persistent Radiopharmaceutical Therapy

Persistent immunoregulatory and apoptosis sensitization agents in a polymer matrix can fill the center of the timed disintegration therapeutic capsule, serving as a 12-month therapeutic reservoir. Essentially all the at risk breast, prostate, or other tumor bearing organ, can be treated by interstitial infiltration with locally persistent, very slowly absorbed, radiopharmaceuticals, such as Phosphocol P-32 (colloidal chromic phosphate P-32, available from Mallinckrodt Inc.), or with other locally persistent tightly bound colloidal formulations, such as palladium-103, iridium-192, iodine-125, gold-198, yttrium-90, tin-117, strontium 85 or 89, or others, typically in a volume centered around the cavity. Mixing such colloidal agents with a suitable protein or synthetic polymer such as collagen-mucopolysaccharide or silk-elastin engineered protein polymers facilitates achieving sustained predictable local controlled persistence. Such tissue infiltration with polymer suspensions of colloidal radiopharmaceuticals can be performed with serial passes of a simple forward deployed multineedle apparatus similar to the cavity cutter. When a therapeutic capsule is to be used, such therapeutic capsule may contain radiopharmaceuticals, preferably in the form of colloids of 3–300 microns diameter of Phosphocol P-32, which will migrate to lymphatics in a controlled manner as the capsule is slowly resorbed by the body. Tissue implantation of such colloidal agents within a suitable protein or synthetic polymer such as collagen-mucopolysaccharide or silk-elastin engineered protein polymers can be performed without creating a therapeutic capsule, if desired. Such strands of formed in place polymer materials may be of thicknesses ranging from 0.05 mm to 5 mm diameter.

Aesthetic Capsules

Breast conserving surgery can advance significantly by use of aesthetic capsules which are formed after negative margin status is assured. Avoiding loss of breast volume can spare many women from breast reduction surgery on the contralateral breast which is often done to restore symmetry. Aesthetic and therapeutic considerations can be combined as desired. Choices of capsule thickness and capsule contents are many.

A detachable, expandable balloon may be placed in the cavity using any approved or approvable balloon wall material as the insertable capsule. The balloon is then filled with any approved or approvable liquid, gel, or polymerizable material for optimum aesthetics. Therapeutic substances can be incorporated in the balloon wall and/or filling materials.

Formed in place aesthetic capsules can be created over a temporarily inflated balloon, which is then withdrawn.

Formed in place aesthetic capsules can be filled with any approvable liquid, gel, or polymerizable material for optimum aesthetics. A patch or plug of preformed capsule material is preferably inserted as a last step. A formed in place capsule patch or plug is also feasible.

Breast augmentation proceedures in the absence of malignancy can be readily performed through a minimal 5 mm incision for trocar placement in front of or behind the pectoralis muscles. After entry into the desired tissue plane, endoscopic dissection of the desired space is accomplished, preferably within a pressurized saline filled space which speeds dissection. Gravity and traction can also be applied to further open potential spaces and free up tissue planes. A formed in place capsule may be created around a suitable inflatable form. Alternatively, in implantable capsule may be preformed and tightly wrapped around the filling tube. Symmetrical augmentation implants can be inserted without internal visual guidance. Ultrasound external monitoring is helpful. Endoscopic staples or sutures can secure the implant to the chosen tissue plane. Capsule forming material can be distributed around a preformed implant to further anchor the implant to adjacent tissues.

Any tissue area chosen can be so augmented, including pectus excavatum, genitals, and facial features.

Aesthetic Surgical Applications.

The use of a small introducer trocar to achieve removal of significant volumes of tissue readily lends itself to liposuction related applications throughout the body. Much more precise anatomical control and much less bleeding are significant advances over previous turgid and ultrasound augmented liposuction technologies. The softer gel resorbable capsule technology for liposuction consists of locally persistent vasoconstrictor and coagulation augmenting agents.

Coexisting Chronic Diseases

Although this disclosure largely focuses on the treatment of malignant diseases in all patients, many patients developing malignancies also have common chronic diseases including: diabetes, atherosclerosis, alcoholism, liver failure, renal failure, collagen vascular diseases, and malabsorption syndromes. In addition, cancer patients can also suffer from the effects of a sedentary lifestyle and/or the effects of impaired wound healing. Many individuals in middle age and virtually all elderly individuals have depressed wound healing compared with healthy 18-year-olds.

Benign diseases can be favorably influenced by release of physiological agonists for desired functions as well as release of antagonists against harmful processes. Upregulation of cellular and humoral immunological functions of lymphatics in malignant diseases may minimize tumor recurrence, minimize infections, and speed complication-free healing. In selected patients in whom curative surgical excision seems assured, careful use of agents promoting wound healing may be employed. Vascular endothelial growth factor and basic fibroblast growth factor are both essential to robust wound repair and may be deficient in patients who have received previous radiation therepy, as well as in aging and debilitated patients. Since these agents stimulate tumor growth, their use in debilitated cancer patients is appropriate only when the risks of inadequate wound healing exceed the risks of tumor recurrence.

Many classes of agonist and antagonist therapeutic agents are suitable for incorporation into therapeutic capsules, sheets, and infiltration materials for use in malignant diseases.

Note that promotion of any desired result can be achieved by (1) an agonist, (2) a blocker of inactivation of the agonist, or (3) a blocker of a physiological antagonist.

Similarly, inhibition of any undesired result can be achieved by (1) an antagonist, (2) a blocker of inactivation of the antagonist, or (3) a blocker of a physiological agonist.

Proteins, peptides, amino acids, antibodies, and molecular recognition units are important in all categories of agonists and antagonists. Conventional drugs and pro-drugs are also important.

Agents to control wound healing, include: growth promoting factors, blockers of inactivation of growth promoting factors, blockers of physiological growth inhibitors, growth inhibitors, blockers of inactivation of growth inhibitors, blockers of growth promoters, coagulants, blockers of inactivation of coagulants, blockers of anticoagulants, anticoagulants, blockers of inactivation of anticoagulants, blockers of coagulants, fibroblast attractants, blockers of inactivation of fibroblast attractants, blockers of fibroblast repellants, fibroblast repellants, blockers of inactivation of fibroblast repellants, blockers of fibroblast attractors, differentiation promoters, blockers of inactivation of differentiation promoters, blockers of physiological differentiation inhibitors, differentiation blockers, antagonists of inactivation of differentiation blockers, blockers of physiological differentiation promoters, angiogenesis promoters, blockers of inactivation of angiogenesis promoters, blockers of physiological angiogenesis inhibitors, angiogenesis blockers, blockers of inactivation of angiogenesis inhibitors, blockers of physiological angiogenesis promoters, angiotensin converting enzyme promoters, blockers of inactivation of Angiotensin converting enzyme promoters, blockers of physiological angiotensin converting enzyme inhibitors, angiotensin converting enzyme inhibitors or blockers, antagonists of inactivation of angiotensin converting enzyme inhibitors, blockers of physiological angiotensin converting enzyme promoters, vasodilator drugs and arginine, and vasoconstrictor drugs and vasopressin.

Virtually all of the categories of drugs can be usefully adapted to locally persistent forms which can be applied under minimal invasive technology. One typical application may be sutures or staples that slowly release anti-fibroblast growth factor materials to prevent keloid formation in patients who are excessively scar prone. Gene based therapy may be delivered in small resorbable pellets made of collagen or other suitable carrier including polyethylene glycol or zinc sponge metal.

Intraoperative Radiation Therapy

Additional options for radiation therapy include the use of new miniaturized radiation therapy technology, which allows intraoperative insertion of a small (in embodiments about 8 mm diameter) tubular device having an ionizing radiation emitting target at the end of the tube. Thus, almost 360 degrees of local radiation of about 10 to 70 keV can be imparted to the fresh tumor excision site.

The insertable therapeutic device tip can be provided with a range of sizes of inflatable high-pressure self-centering balloons to allow exact centering of the radiation emitting tip within the cavity created by the instant encapsulation technology, without requiring enlargement of the entrance channel. Moreover, the balloons can be filled with selective low energy radiation filters in the form of liquid solutions which prevent radiation overdosage to the innermost cavity. Colloidal suspensions of copper in an appropriate viscosity intrinsically safe liquid vehicle both effectively filter low x-ray energies and re-radiate characteristic copper x-rays in all directions, enhancing uniformity of the radiation field. Because the intensity of ionizing radiation falls off with the square of the distance from the source, centering is critical to avoid underexposure and overexposure. The technology currently employs hollow rigid spherical plastic attachments for centering which is accomplished by suturing the open cancer excision cavity over the sphere with purse string sutures.

Hyperthermia And Imaging

Colloidal iron or copper particles should be visible as a cloud on ultrasound, MRI and x-ray images. Such suspensions couple well with electromagnetic fields, leading to ease of energy deposition for heating. Such suspensions dispersed in a capsule forming mixture, or dispersed throughout tissues adjacent to the tumor excision bed serve multiple functions, including: (1) image contrast, (2) catalysis of cross-linking of collagen and mucopolysaccharide or glycosaminoglycan components of capsule wall and within tissues, (3) electromagnetic field coupling for heat generation for local hyperthermia, which further cross-links the capsule materials and allows therapeutic increases in local temperature throughout tissues infiltrated with metallic colloids and persistent solutions and suspensions, (4) strong absorption of specific light wavelengths, allowing laser energy coupling to capsule and/or to tissues, and (5) persistent radiation and chemotherapy sensitization of exposed tissues with particles in long term equilibrium with tissue fluids, creating and maintaining local saturated metal ion tissue fluid solutions.

Locally Persistent Radiation Sensitizers

The oncology application is particularly exciting because copper and iron ions participate as catalysts in DNA damage. The nature of a catalyst is that it is not used up in the reaction. Locally persistent high concentrations of copper and iron serve to sensitize tissue to ionizing radiation and to chemotherapy. Metals have higher atomic numbers than tissues and so have a higher likelihood to interact with ionizing radiation.

Phagocytosis by white cells releases $H_2O_2$, which reactivates the free radical cascade. Some catalytic ions are carried away by blood flow or diffusion and some become bound in very stable complexes. Thus, continual local replenishment is needed to extend local therapeutic effect over months.

Histidine as a Radiation and Chemotherapy Sensitizer

Single strand DNA breaks caused by copper or iron catalyzed free radical reactions, by x-rays or beta particles or by chemotherapy, are perhaps ten times more common than double strand breaks. Even a low local concentration of the amino acid histidine effectively converts single strand DNA breaks into the much more lethal double strand breaks, and higher concentrations are even more effective. Ascorbate interacts with the iron and copper to reduce $Fe^{+3}$ to much more diffusible $Fe^{+2}$ and $Cu^{+2}$ to more toxic $Cu^+$ which themselves create single strand and double strand breaks and other DNA damage, especially in conjunction with ionizing radiation and free radical promoting chemotherapy agents. Interactions between ascorbate and catalytic metals are discussed in Buettner et al., "Catalytic Metals, Ascorbate and Free Radicals: Combinations to Avoid," Radiation Res. 145: 532–41 (1996).

Histidine transformation of single strand DNA breaks into far more lethal double strand breaks creates the potent cytotoxicity of histidine, as documented by Cantoni et al. in "Cytotoxic Impact of DNA Single vs. Double Strand Breaks in Oxidatively Injured Cells," Arch. Toxicol. Suppl. 1996;18:223–35. Cantoni et al. observed that low and high concentrations of hydrogen peroxide kill cells by different mechanisms. Importantly, they found that 80 micromoles of hydrogen peroxide destroyed more than 50% of DNA if 300 micromoles of l-histidine were present versus no injury in the absence of histidine. Further, cell lines resistant to hydrogen peroxide were rendered sensitive by the presence of l-histidine. This attribute may be of great importance in overcoming the radiation resistance of hypoxic tumor cells.

Histidine is a special case of a free radical protecting and promoting agent, according to Chevio, "A site-specific mechanism for free radical induced biological damage: The essential role of redox-active transition metals," Free Radicals in Biology and Medicine, Vol. 5: 27–37, 1988. It is an effective hydroxyl radical scavenger, even at low concentrations. Histidine is an effective chelator for copper and iron. Histidine changes characteristics in the presence of higher concentrations of copper and iron beyond its chelating limits. Histidine also forms a tight complex with hydrogen peroxide. Histidine is an efficient donor of hydrogen atoms.

Thus, histidine can perform opposite protective or lethality enhancing roles, depending on presence of new or pre-existing single strand DNA breaks and specific concentrations of metal ions.

Histidine-pyridine-histidine-3 (HPH-3) is an oxygen-activating ligand based on the structure of bleomycin. HPH-3 induced the death of human pancreatic adenocarcinoma AsPC-1 cells in 24 hours, causing apoptotic morphology and internucleosomal degradation of DNA. HPH-3-induced cell death was not inhibited by antioxidants such as reduced glutathione and N-acetylcysteine, whereas hydrogen peroxide-induced cell death was inhibited by them, indicating that hydrogen peroxide is not involved in the induction of apoptosis by HPH-3. Induction of apoptosis by HPH-3 was inhibited by zinc and copper ions, indicating that chelation with ferrous ion is responsible for induction of apoptosis, as is the case in chelation by bleomycin to cleave DNA. Bleomycin A2 and its fragment having no DNA-binding region, glycopeptide-3, did not induce apoptosis in AsPC-1 cells. Bleomycin A2 induced G2/M block in flow-cytometric analysis, but HPH-3 did not and instead induced an apoptotic pre-G1 peak. Thus, HPH-3 induced apoptosis in human pancreatic carcinoma cells, which is a unique characteristic among bleomycin-related compounds. This work by K. Umezawa appeared in "Induction of apoptosis in human pancreatic carcinoma cells by a synthetic bleomycin-like ligand," 89(9) Jpn. J. Cancer Res 947–53 (September 1998).

Persistent resorbable formulations, including ingredients such as iron dextran, ascorbate, Phosphocol P-32, copper, histidine, and angiogenesis inhibitor, which release colloidal particles during dissolution may be employed for locoregional lymph node treatment in breast, lung, prostate, pancreatic and colorectal carcinomas. Persistent capsules can be engineered to release colloidal particles which will migrate to and treat locoregional lymph nodes by multiple mechanisms.

The amino acid histidine efficiently converts single strand breaks into double strand breaks, dramatically enhancing lethal effect. Administration even hours after the irradiation is effective. Polymerization of histidine can result in large molecular weights. Co-polymerization of histidine-Cu-histidine-Cu-histidine-Cu- is attractive. The molecular weight 26,000 has been reported for plain poly-histidine; however, larger polymerizations are possible. For comparison, albumin has a molecular weight around 75,000.

The advantage of combining iron and copper in the same dosage form includes the fact that iron and copper have separate mechanisms of DNA damage as well as that the combination of two metals forms a natural battery when wetted by body fluids leading to the controlled dissolution of the dosage form.

When iron or copper are closely associated with DNA, site specific reactions can result in single chain breaks and double chain breaks. The maximum lethality per mole of iron or copper is achieved by site specific DNA damage from chemical reactions of iron or copper molecules closely associated with the DNA. There is excellent published experimental evidence that ferritin at 32 micrograms per ml is a nontoxic radiation sensitizer that does not become toxic until 48 micrograms per ml and higher levels are reached. Normal serum contains 1 to 2 micrograms/ml of iron, primarily bound to transferring.

Colloidal iron or copper nanoparticles in equilibrium with saturated metal ion solutions can be incorporated into sutures and stables forming structures that should be visible on ultrasound, MRI and x-ray images. Such suspensions couple well with electromagnetic fields leading to ease of energy deposition for heating. Such suspensions dispersed in a suture forming mixture and staple coating mixtures serve multiple functions, including: (1) image contrast, (2) catalysis of cross-linking of collagen and mucopolysaccharide or glycosaminoglycan components, (3) electromagnetic field coupling for heat generation, (4) strong absorption of specific light wavelengths, and (5) persistent radiation and chemotherapy sensitization of exposed tissues.

Safety of local iron administration is considerably increased when local deposition is combined with periodic administration of systemic iron chelators to prevent elevation of serum iron and consequent stimulation of metastases distant from the therapeutic persistent formulation site. Amino acids, peptides, and proteins, including histamine, histidine, bradykinin, vasopressin, as well as interleukins and cytokines, can be locally released to stimulate or suppress targeted cellular functions. In some cases, persistent vasoconstrictor materials may be appropriate, especially in the area of oncology surgery. Such vasoconstrictor releasing capsules may be valuable for surgery on highly vascular structures such as liver.

If complete surgical tumor excision is impossible, residual tumor is treated by local infiltration of radiation sensitizers and/or therapeutic deposition of radiation sensitizers and other tumor killing agents in a timed release artificial capsule. In those cases in which residual tumor cells are adjacent to vital structures or tumor cell spread to adjacent tissue is likely, persistent chemical agents can be provided by direct injection and by incorporation in a specially formed therapeutic capsule wall for timed release to potentiate chemotherapy and radiation therapies. Radiation sensitization by metal catalyzed free-radical reactions can increase cancer cell destruction. Iron and copper compounds and colloids can be infiltrated into at-risk tissues by multiple closely spaced injections, or introduced into the retained capsule wall in order to potentiate other therapies such as systemic chemotherapy, non-ionizing radiation, ionizing radiation, and ultrasound energy deposition. The potential utilization of iron and copper salts as radiation sensitizers is novel. Radiation sensitizers include atoms having atomic numbers higher than the atoms in tissue, favoring greater interaction with the x-ray beam. A 30% increase in tumor radiation sensitivity allows much higher cancer cure rates with much lower damage to normal tissues. Moreover, iron and copper are intrinsically highly catalytic for free-radical reactions, especially when ionized by incident x-rays. These metals may also be activated by ultrasound energy, and potentially by laser energy.

When the formulations are being used for post-operative therapy or for treatment outside of the capsule, they are preferably locally persisting, so as to concentrate their effects where most needed. For example, iodine compounds used for conventional x-ray contrast can be reformulated as colloids or small particles which can remain in the tissues long enough to facilitate-radiation therapy treatments lasting many weeks.

Tumor killing effectiveness of each unit of absorbed radiation can be greatly enhanced by maximizing formation and propagation of the free-radical reactions initiated when ionizing radiation knocks electrons off target molecules. Iron and copper are potent catalysts for free-radical reactions within the living body. Iron and copper also have atomic numbers greater than tissue, increasing the likelihood of interaction with the radiation therapy beam. The invention also encompasses the prophylaxis and treatment of local and regional lymphatic vessels and nodes with extended release forms of biological response modifiers, iron and copper compounds, and extended release forms of conventional cancer chemotherapeutics, infiltrated into tissues surrounding the removed capsule wall or slowly released from biodegradable resorbable capsule wall. Physical ultrasound interaction of metallic powders and colloids produces surface chemical activation of intrinsically catalytic compounds serving to greatly amplify the direct physical tissue destruction effects of ultrasound energy. The artificial capsule can be formulated to include a wide range of physical, chemical and/or biological therapeutic agents which are slowly released (i.e., sustained-release agents) to provide local tissue treatment and locoregional lymphatic treatment.

Collateral damage to normal tissues adjacent to cancerous tumors also limits the effectiveness of radiation therapy. Radiation sensitizers have been sought to selectively increase damage to malignant tissues while sparing healthy tissues. Unfortunately, these radiation sensitizers can themselves be toxic to healthy tissues when injected at levels high enough to achieve their radiation enhancing effect, and/or might not persist in the area of the tumor for a time sufficient to enhance the effect of radiation on the tumor.

It is generally recognized that transition metals, including $Cu^+$, $Fe^{2+}$, $Sn^{3+}$, $Co^{2+}$ and $Ni^{2+}$, have all been demonstrated to be a source of catalysis of free-radical reactions in biological systems. Thus, the tumor sterilization and destruction-digestion-fragmentation can be achieved by oxidation by iron or copper catalyzed free-radical chemical reactions, including sodium hypochlorite bleach or hydrogen peroxide free-radical reaction initiating and sustaining compounds. $Cu^{2+}$ associates with the guanine-cytosine base pair of DNA to create local free-radical damage to the DNA characteristic of attack by hydroxyl ion. Copper is a powerful promoter of free-radical damage to lipids, proteins, and especially to DNA and its bases. See Aruoma, "Copper ion-dependent damage to the bases in DNA in the presence of hydrogen peroxide," Biochemical Journal 1991, 273: 601–4.

Neither copper nor iron ions can exist free in aqueous solutions at pH 7.4, partly because body fluids contain phosphate and bicarbonate ions and any available metal ions must bind to biologic molecules. Damage caused when metal ions react with hydrogen peroxide to form hydroxyl radical will thus be directed to the site of metal ion binding.

The biologic implications of site specificity of hydroxyl ion formation are profound. $Fe^{2+/3+}$ reacts with super oxide anion, $\bullet O_2^-$ and hydrogen peroxide via the Haber-Weiss mechanism to generate extremely reactive hydroxyl radicals.

Iron-catalyzed injury results in damage to cell constituents, including oxidative damage to lipid membranes, proteins, nucleic acids, mitochondria, lysosomes, and the sarcolemmal membrane. Many pathological events are thought to be associated with peroxidation of lipids in biological membranes. This peroxidation proceeds by a free-radical chain reaction (1–3):

$$LH \rightarrow L\bullet \quad (1)$$

$$L\bullet + O_2 \rightarrow LOO\bullet \quad (2)$$

$$LOO\bullet + LH \rightarrow LOOH + L\bullet \quad (3)$$

where $LOO\bullet$ is the lipid peroxy radical.

The initiation reaction 91) is one of the key steps. Iron is a well-known catalyst of initiation step (1), and iron-oxygen species have been suggested to be responsible for initiation of peroxidation. However, it has been pointed out that since biochemical membrane systems also contain traces of pre-formed lipid peroxide (LOOH), added iron is more likely to stimulate peroxidation by decomposing lipid peroxide to the alkoxy radical ($LO\bullet$) (4) than by generating initiating species.

$$LOOH + Fe^{2+} \rightarrow LO\bullet + Fe^{3+} + OH^- \quad (4)$$

$$LO\bullet + LH \rightarrow LOH + L\bullet \quad (5)$$

LOOH-dependent lipid peroxidation plays an important part in oxidative deterioration of biological membranes.

Goldstein et al., in "Transition metal ions and oxygen radicals," Int. Rev. Exp. Pathol. 31: 133–64, 1990, proposed a "site-specific" Fenton mechanism in which the binding of a transition metal ion to the biological target is a prerequisite for the production of OH radical-mediated cell damage.

Schaich et al., in Lipids 23: 570–79, 1988, proposed that the solubility of iron complexes in the lipid phase of membranes is a critical determinant of their catalytic effectiveness in initiating lipid peroxidation. Iron ions likely arrest cell growth by chemically generating hydroxyl radicals from lipid peroxides.

Treatment of locoregional lymphatics may be performed by inclusion of therapeutic colloids and slow release chemical formulations within the materials forming the capsule wall and/or by direct injection of therapeutic materials outside the capsule wall. Such therapeutic substances may include conventional antineoplastic agents, including colloidal forms of such agents designed for sustained-release and preferential lymph node targeting. Suitable therapeutic substances include colloidal radioactive agents, hormonal agents, biological growth modifiers, growth factor blocking agents, DNA transacting viral probes, and free-radical catalytic chemical means.

Iron dextran is a U.S. Food and Drug Administration approved injectable agent formulated for intravenous or intramuscular injection. A suitable dose is about 100 milligrams of iron in 1 milliliter of volume.

The possibility of using iron compounds as radiation sensitizers was disclosed in abstract form by Nelson et al. in 24 Cell Proliferation 411 (1991):

Although 32 micrograms/ml ferritin was not toxic, it reduced clonogenic-cell survival after x-irradiation by approximately 75%, from about 0.66 to 0.17 at 4.0 Gray. But, at doses above 48 micrograms/ml, toxicity increased appreciabilty in a dose dependent manner.

This work subsequently appeared as a full paper entitled "Ferritin-iron increases killing of Chinese hamster ovary cells by x-irradiation" in Cell Proliferation 1992 25:579–585.

This work has attracted little notice and has never been tried as therapy in human beings. A significant problem with the use of iron as a radiation sensitizer involves the property of stimulating tumor growth at sub-toxic iron concentrations as documented by Stevens et al. in Iron, Radiation, and Cancer. Environmental Health Perspectives 87:291–300, 1990. Thus, the prior art teaches that growth of metastases outside the radiation field will be stimulated at the same time that cell killing inside the primary tumor is increased, yielding an unacceptable tradeoff.

The current invention overcomes this difficulty by teaching the local administration of persistent timed release (i.e., sustained release) forms of iron such as iron dextran supplied as 100 milligrams/ml in the vicinity of the tumor in conjunction with systemic administration of iron chelating agents. Concentrations of iron that are directly tissue toxic, far in excess of 48 micrograms/ml, are released locally from the iron dextran. By the combination of direct tissue iron toxicity, and local radiation sensitization within the diffusion zone surrounding the persistent iron dextran, significantly increased tumor control can be achieved. Addition of systemically administered iron chelating agents by periodic intravenous administration provides protection against the metastasis growth promoting effects of elevated systemic iron levels.

There are several tumors which kill primarily by local invasion, such as brain glioblastoma multiforme and pancreatic cancer, and in which the role of metastatic disease is minimal. Such carefully selected tumors may benefit from local tissue iron toxicity and local radiation sensitization, without the necessity of systemically administered iron chelating agents. Tumors with any metastatic potential are best treated with systemically administered iron chelating agents.

If the radiation enhancing material is, for example, injected directly into the prostate gland through the rectal wall, the prostate would be diffusely labeled and some iron dextran would flow out into lymphatics draining the prostate. Thus, the intra prostate cancer area as well as the lymphatics that may harbor spread of prostate cancer can both receive the benefits of enhanced radiation therapy effectiveness when those areas are treated.

Similarly, if iron dextran or other persisting iron/copper compounds are directly injected into lung cancers or other solid tumors through CT, MR or ultrasound guided needles in a technique resembling needle biopsy, the benefits of this radiation sensitization technique could extend to all solid tumors.

Iron dextran or other persisting iron/copper compounds can also be deposited into tumors through bronchoscopic methods, or by angiographic injection into feeding arteries. Injection into the portal veins of the liver may be useful for some tumors. Direct lymphatic injections may also be useful.

Ferricenium salts can act as radiosensitizers of hypoxic cells. The toxicity of these metal complexes, but not their radio-sensitizing ability, is reduced by including serum albumin in the medium. See, e.g., Joy et al., in J. Radiation Oncology Biol. Phys., 16: 1053–56, 1989 and Teicher, et al., in Radiation Research 109: 36–46, 1987.

U.S. Pat. No. 5,246,726 discloses oral administration of an essential fatty acid along with oral administration of iron. It does not mention the possibility of intravenous preparations of fatty acids in which appropriate daily doses are given by intravenous administration of fatty acid emulsions coupled with daily doses of iron given either in the same preparation of or by another route, for example, iron dextran or iron sorbitol preparations for intramuscular injection in the treatment of persons suffering from cancer. The patent discloses that the cancer cell killing effect of fatty acids is dramatically enhanced when the fatty acids are provided to cancer cells in the presence of iron within a culture. There is no use of ionizing radiation in the patent.

Lesnefsky, "Tissue Iron Overload and Mechanisms of Iron-Catalyzed Oxidative Injury," in *Free Radicals in Diagnostic Medicine*, pp. 129–146 (Plenum Press, N.Y. 1994), points out that the heart is the most susceptible organ to damage in iron overload states, sustaining injury at approximately one thousand micrograms of iron per gram of tissue. Iron is essentially insoluble in physiological buffers. As the recommended usual dose of iron dextran is 100 milligrams of iron in 1 milliliter of volume, there is a significant therapeutic to toxic ratio of 10 to 1, sparing uninvolved tissues and yet sensitizing tumors and draining lymph nodes to radiation therapy.

Iron bound to negatively charged ligands including citrate, ammonium citrate, nitrofluoracetic acid, or adenosine diphosphate has increased solubility which enhances the redox-cycling iron, allowing iron to catalyze oxidative damage. Redox-cycling by iron between $Fe^{2+}$ and $Fe^{3+}$ damages biomolecules. $Fe^{2+/3+}$ reacts with super oxide anion and hydrogen peroxide via the Haber-Weiss mechanism to generate extremely reactive hydroxyl radicals.

Super oxide anion or ischemia can radioactively release iron from ferritin into the redox-active cytosolic pool. Iron is present in ferritin as $Fe^{3+}$, and reduction to $Fe^{2+}$, either by $O_2$-ascorbate, or other mechanisms, results in the release of iron into pools that can catalyze oxidative injury. Similarly, during oxidative stress, hydrogen peroxide can release iron from hemeproteins, exacerbating oxidative damage. Ischemia causes approximately a 10–20 nM increase in cytosolic iron.

Acidic environments caused by ischemia or inflammation can result in the release of iron from Tf, even at physiologic levels of iron saturation.

Reodx-cycling by iron between $Fe^{2+}$ and $Fe^{3+}$ damages biomolecules, causing cell injury. $Fe^{2+/3+}$ reacts with super oxide anion and hydrogen peroxide via the Haber-Weiss mechanism to generate the very reactive hydroxyl radical. The second reaction between $Fe^{2+}$ and hydrogen peroxide that generates ●OH is the Fenton reaction.

The generation of "free" hydroxyl radical may not actually occur. Instead, a highly-reactive "crypto" hydroxyl radical in the iron coordination complex, perhaps the preferryl ion, may be the oxidizing species. Iron-catalyzed hydroxyl radical formation requires at least one aqueous coordination site in the iron coordination sphere.

Iron ligands such as EDTA, sugars, citrate, and nucleotides (including ATP and ADP) allow water in the iron coordination complex and catalyze subsequent iron-catalyzed ●OH formation.

Haber-Weiss Reactions:

Fenton reaction:

In the cell, ●OH causes oxidative damage to DNA, membrane lipids, and proteins. Protein damage can involve protein sulfhydryl oxidation, carbonyl group formation, or oxidative bond cleavage. Protein damage leads to enzyme inactivation, structural protein alteration, and often accelerated proteolysis. Oxidative DNA damage causes strand breaks and cross-linking, as well as the hydroxylation of bases, the latter providing a marker of oxidative damage to DNA. By any of these mechanisms, oxidative damage to DNA increases the incidence of mutations. Iron can both initiate and propagate lipid peroxidation, leading to altered membrane fluidity, inactivation of membrane-bound enzyme complexes, and eventual membrane disruption.

$Fe^{2+}$ bound to ADP and ATP is an especially good catalyst for ●OH generation, and of potential physiologic importance as well. The Fenton reaction between $Fe^{2+}$, -ADP and hydrogen peroxide clearly damages tissues.

While the Haber-Weiss and Fenton reactions have been widely considered as potential causes of iron-catalyzed lipid peroxidation, the ability of iron to cause oxidative damage by redox-cycling independent of oxygen metabolites has also been described. $Fe^{2+}$-ADP chelates alone cause oxidative damage to myocardial lipids, and the lag phase prior to the initiation of oxidative damage is reduced by the presence of small amounts of $Fe^{3+}$. $Fe^{3+/3+}$ ratios of 1:1 to 7:1 result in the highest rates of lipid peroxidation.

Complexes of iron with molecular oxygen may be the active species. The potential for similar direct non-oxyradical mediated iron-redox cycling to damage proteins or DNA has not been adequately explored.

$Fe^{2+}$-ADP is an efficient initiator, but does not result in propagation. However, $Fe^{2+}$-EDTA is an efficient propagator of lipid peroxidation. Thus, iron could be involved in damage to cell membrane lipids in at least three ways: (1) iron-generated ●OH could initiate lipid peroxidation (2) iron could initiate lipid peroxidation independent of ●OH; or (3) iron could propagate lipid-radical chain reactions via lipid peroxide decompositions independent of ●OH.

Exposure of rat liver mitochondria in vitro to 1–3 mM $Fe^{2+}$-chelates increases lipid peroxidation and progressively inhibits electron transport. The probable mechanism involves iron catalyzed oxidative damage to mitochondrial membrane lipids, with alteration of the inner membrane environment, and subsequent inhibition of the membrane associated enzymes of the electron transport chain.

Even prior to the onset of electron transport defects, subtle iron overload increases mitochondrial lipid peroxidation and calcium release. Mitochondrial calcium release initiates subtle cycles of calcium uptake and release from mitochondria that consume energy and impair cellular calcium homeostasis, predisposing to cell damage.

The primary importance of intracellular iron stores is as the catalytic site of oxidative damage during reperfusion. The ●$O^{2-}$ and hydrogen peroxide precursors of iron-catalyzed injury can be generated either internal or external to the cell, yet still participate in intracellular iron-catalyzed oxidative damage.

Hydrogen peroxide can diffuse across cell membranes, while super oxide can traverse anion channels. This finding is consistent with results in cell culture that target cells provide the intracellular iron for their own destruction, even when ●$O^{2-}$ and hydrogen peroxide are generated in the extra cellular space.

Increased redox-active iron present in hemeproteins and the cytosolic iron pool can catalyze oxidative damage to lipids, proteins, and nucleic acids, either by oxyradical dependent or independent mechanisms.

Iron-catalyzed injury results in damage to cell constituents, including mitochondria, lysosomes, and the sarcolemmal membrane. These mechanisms of iron-mediate damage are involved in the pathogenesis or organ dysfunction in primary hemochromatosis, transfusion-related iron overload, ischemia-reperfusion injury and cardiac anthracycline toxicity.

DNA, cellular proteins, lipid membranes, mitochondria and other cellular organelles are targets for molecular damage caused by either covalent binding of primarily electrophilic, but in some cases free-radical, reactive intermediaries and direct free-radical initiated oxidative stress resulting in target oxidation.

Castilho et al., in Archives of Biochemistry and Biophysics, Vol. 308, No. 1, January, pp. 158–163, 1994, have reported on oxidative damage of mitochrondria induced by Fe(II)citrate is potentiated by $Ca^{2+}$ and includes lipid peroxidation and alterations in membrane proteins. Both oxygen radical formation and $Ca^{2+}$ seem to be involved in the overall process of cell injury associated with oxidative stress. The mitochondria is an important cellular site of both generation of oxygen radicals and oxidative damage. It is well known that iron complexes induce extensive lipid peroxidation and irreversible damage in isolated mitochondria. Iron citrate can shift the $Fe^{3+/2+}$ couple reduction potential from +0.77V to +0.33V, which causes a high rate of $Fe^{2+}$ auto-oxidation. Castilho et al. conclude that $Ca^{2+}$ potentiates the oxidative damage of mitochondria caused by $Fe^{2+}$ citrate.

Fujii et al. recently reported on site-specific mechanisms of initiation by chelated iron and inhibition by alpha-tocopherol of lipid peroxide dependent lipid peroxidation in charged micelles. See Archives of Biochemistry and Biophysics 284: 120–126. 1991.

In addition to the pathological events discussed above, which are thought to be associated with peroxidation of lipids in biological membranes, added iron reacts with the OOH-group of LOOH at the membrane surface to form LO●, and the LO● then penetrates into membranes and reacts with the unsaturated bonds of LA to initiate the chain reaction in a deep inner phase, where LOO● is generated.

Gutteridge has reported on "Ferrous-salt-promoted damage to deoxyribose and benzoate" in Biochem. Journal (1987) 243: 709–714.

Quinlan et al., in the paper, "Action of lead(II) and aluminum(III) ion on iron-stimulated lipid peroxidation in liposomes, erythrocytes and rat liver microsomal fractions," Biochemica et Biophysics Acta, 962: 196–200, (1988), found that aluminum $Al^{3+}$ ions increase $Fe^{2+}$ dependent liposomal peroxidation at pH 7.4 and at pH 5.5. Thus, this powerful effect is found over a concentration of 10 mM to 400 mM, and over acidic to alkaline pH values. The $Fe^{2+}$ is largely acting by decomposing traces of preformed lipid peroxides in the membrane fractions to give chain propagating peroxyl and alkoxy radicals.

$Al^{3+}$ ions in aqueous solution undergo extensive hydrolysis at pH 7.4. Quinlan et al. hypothesize that $Al^{3+}$ binds to the membrane surface, thus causing a localized freezing of phospholipid movement, facilitating the propagation of peroxidation. This work suggests that aluminum sulfate in concentrations of 10 mM to 400 mM in conjunction with ferrous ammonium sulfate at 100 mM produces catalytic effects. Phagocytic cells, such as monocytes and macrophages, may become activated by contact with foreign compounds and foreign particles in the treated tissue. Activated phagocytic cells produce toxic metabolites of oxygen coupled with the release of granular enzymes and the formation of highly reactive metabolites such as hypochlorite. The entire range of white cells, including polymorphonuclear leukocytes, T-cells, basophils, eosinophiles, monocytes and macrophages, can be involved in tissue injury reactions. Such reactions may serve to initiate further propagation of oxidative free-radical injury.

Hydroxyl radicals are produced in living organisms by at least two mechanisms: (1) reaction of transition metal ions with hydrogen peroxide, and (2) homolytic fission of water caused by ionizing radiation. Hydroxyl radicals are extraordinarily reactive and attack all biologic molecules, usually setting off free-radical chain reactions. Transition metals, including $Sn^{3+}$, $Cu^+$, $Fe^{2+}$, $Co^{2+}$ and $Ni^{2+}$, have all been demonstrated to be a source of catalysis of free-radical reactions in biological systems. $Cu^{2+}$ associates with the guanine-cytosine base pair of DNA to create local free-radical damage to the DNA characteristic of attack by hydroxyl ion.

Different ligands to $Fe^{2+}$ may stabilize this intermediate so that little hydroxide ion is formed, whereas others destabilize it. Iron ethylenediaminetetraacetic acid chelates are good sources of hydroxyl ion in the presence of hydrogen peroxide. Interestingly, the relatively slowly reactive $Fe^{3+}$, when interacting with ascorbate (Vitamin C), yields very highly reactive $Fe^{2+}$ and semi-dehydroascorbate. Thus, iron salt-ascorbate and hydrogen peroxide produces abundant radicals. Aruoma et al., in the Journal of Biochemistry 264: 20509–12, 1989, documented "Damage to the bases in DNA induced by hydrogen peroxide and ferric iron chelates." They documented that ferric nitrilo tri-acetic acid produced the most DNA damage in the presence of hydrogen peroxide. Nitrilo tri-acetic acid was previously a common constituent of detergents and is now widely distributed in the environment.

Organisms take great care in the handling of iron, using both transferring transport protein and ferritin and hemosiderin storage proteins to minimize the amount of "free" iron within cells and in extra-cellular fluids. This sequestration of transition metals is a very important contribution to antioxidant defenses. However, oxidative stress itself can provide iron for free-radical reactions. •$O2^-$ can mobilize iron from ferritin, and hydrogen peroxide can degrade. Copper is a powerful promoter of free-radical damage to lipids, proteins, and especially to DNA and its bases. See Aruoma "Copper ion-dependent damage to the bases in DNA in the presence of hydrogen peroxide." Biochemical Journal 1991, 273: 601–604.

The concentration of iron of copper ions catalytic for free-radical reactions within the body is extremely low because metal ion sequestration is highly effective. Neither copper nor iron ions can exist free in aqueous solutions at pH 7.4, partly because body fluids contain phosphate and bicarbonate ions. Any available metal ions must bind to biologic molecules. Damage caused when the react with hydrogen peroxide to form hydroxyl radical will thus be directed to the site of metal ion binding. The biologic implications of site specificity of hydroxyl ion formation are profound. The type of biologic damage produced by site specific free hydroxyl radical generation will not resemble that produced by attack of free hydroxyl ions generated by ionizing radiation. This has been documented in Von Sonntag, "The chemical basis of radiation biology" 1987.

Once tissue injury has been initiated by a free-radical cascade, additional injury mediators, such as prostaglandins, leukotrienes, interleukins, interferson, and tumor necrosis factors, may all play additional roles. White cells, especially phagocytes, also play an important role in furthering tissue injury. If bleeding is induced by injury to the walls of blood vessels in the tumor area, free hemoglobin is exposed to excess hydrogen peroxide producing heme degradation with further release of catalytic iron ions. Free heme is also a toxic agent.

Thus, an object of this invention in addition to providing artificial capsules for treating tumors is to selectively increase tissue destruction either by more efficient coupling with the energy field being deposited or in order to propagate chemical reactions that are induced by the deposition of ionizing radiation. Specifically, free-radical reactions can be propagated by the presence in tissue of elemental iron or copper, especially of selected valences. Iron or copper ions and/or colloids can serve to profoundly alter the electromagnetic characteristics of tissue, thereby allowing more effective coupling of the ionizing radiation energy with the volume of tissue containing such increased concentrations of selected high atomic number catalytic materials.

A particularly preferred method of the invention comprises:

A. Preoperative, intraoperative and postoperative infusion of biological agents and pharmaceuticals to kill free floating cancer cells and to block implantation of shed tumor cells and to neutralize growth factors created by the surgical wound.

B. Monitoring the appearance of tumor cells in the peripheral blood during the entire biopsy and the entire surgical procedure.

C. Bipolar needle coagulation under Doppler ultrasound guidance to block arteries and veins surrounding the tumor from all sides and underneath.

D. Clogging lymphatics and compressing lymphatics and venules with adequate volumes of local infiltrated fresh whole blood, and constricting peritumoral vessels with vasoconstrictors such as 1:800,000 epinephrine.

E. Cutting a complete channel around the entire tumor including at least a 5 to 10 mm margin of apparently normal tissue.

F. Filling the channel with the patient's fresh plasma with added collagen and copolymers, and possibly with the patient's concentrated fibrinogen.

G. Inspecting the capsule thus formed by imaging ultrasound, and thickening any apparently thin areas.

H. Injecting absolute ethyl alcohol to kill and dehydrate cells within the created capsule, followed by povodine-iodine to further sterilize the contents.

I. Mechanically fragmenting the tumor by means such as high power ultrasound with aspiration, resectoscope and/or vacuum associated recessed blade cutting instruments.

J. Chemically digesting the remaining cellular debris and flushing-out with suitable sterilizing solutions such as absolute ethyl alcohol and provodine-iodine and absolute ethyl alcohol solutions of iodine. These solutions may be heated to further speed cell killing.

K. Visually inspecting the interior of the capsule with an endoscope.

L. Incising and peeling away the artificial capsule wall.
M. Cauterizing bleeders under endoscope control or inflating a foley catheter balloon within the wound to stop bleeding.
N. Irrigating wound with physiological saline solution.
O. Obtaining touch preparation from the entire internal surface of the surgical site.
P. If touch preparations are negative, internal resorbable purse string sutures can be provided to obliterate the cavity. A solution of povidone-iodine diluted 1:10 with isotonic saline can be applied to potentially diminish local recurrence. Timed-release minocycline can be applied to opposite growth factors.
Q. If touch preparations are positive, the following options are appropriate;
   a. Re-excision of a larger volume, possibly after purse string sutures to obliterate the cavity.
   b. Local infiltration of persistent radiation sensitizers such as colloids of iron and copper.
   c. Deposition of a therapeutic capsule wall or cavity implant providing long term timed release of radiation sensitizers, such as colloids of iron and copper.

Obviously, there is a need to minimize scarring at the area of tissue destruction. One way in which this may be achieved is by preventing significant hemorrhage into the cavity. Prevention of hemorrhage into the cavity may be achieved by installation of certain substances, such as fibrin, in order to limit the total volume of bleeding by rapidly initiating coagulation with minimal amounts of blood. Similarly, irrigation with suction through the needle until such time as no free blood is recovered through the needle lumen can serve to avoid having a post-operative clot form. In general, the smaller the amount of retained blood at the site of operation, the less the subsequent tissue lump formation, and the lower the release of platelet derived growth factor. Imaging through the trocar can be the final step in the sequence assuring that a clean would is left behind.

It is possible to staple, sew and/or chemically bond the cavity walls together, if this is desired, through the same access wound using technologies similar to those found in laparoscopic surgery. In general, the current field of laparoscopic surgery relies upon human vision through a video link. The emerging field of needle/catheter ablation relies predominantly on indirect vision using displays that create images by modalities which are not native to human sensing, such as magnetic resonance, ultrasound, x-ray, unclear, electrical impedance and imaging by infrared and other non-visible wavelengths of the electromagnetic spectrum.

While the invention has been described in detail and with reference to specific examples thereof, it will be apparent to one skilled in the art that various changes and modifications can be made therein without departing from the spirit and scope thereof.

What is claimed is:

1. A method for conducting an operation on a living organism, said method comprising:
   providing a channel around a tissue of said organism;
   infusing into said channel an encapsulating composition to encapsulate said tissue in a capsule; and
   evacuating said capsule of its contents including said tissue;
   wherein said capsule impedes materials encapsulated therein for migrating outside said capsule.

2. The method of claim 1, wherein said encapsulating composition comprises silk-elastin engineered protein polymers.

3. The method of claim 1, wherein said encapsulating composition comprises a hyaluronan.

4. The method of claim 1, wherein said encapsulating composition comprises histidine.

5. The method of claim 1, further comprising dispensing a therapeutic composition into said channel before said encapsulating composition sets within said channel to form said capsule.

6. The method of claim 5, wherein said therapeutic composition comprises a hyaluronan.

7. The method of claim 5, wherein said therapeutic composition comprises a radiation sensitizer.

8. The method of claim 7, wherein said radiation sensitizer is selected from the group consisting of iron and copper.

9. The method of claim 5, wherein said therapeutic composition and said encapsulating composition comprise histidine.

10. The method of claim 5, wherein said therapeutic composition is a locally persisting formulation comprising at least one member selected from the group consisting of biologically active agonist hormones, biologically active antagonist hormones, proteins, peptides, amine acids, biological response modifiers, gene therapy agents, angiogenesis agents, chemotherapeutics and colloidal radiopharmaceuticals.

11. The method of claim 5, wherein said therapeutic composition is a locally persisting formulation comprising colloidal chromic phosphate P-32.

12. The method of claim 5, wherein said therapeutic composition and said encapsulating composition comprise a colloidal metal suspension, and said method further comprises heating said therapeutic and encapsulating compositions by applying radiant energy thereto.

13. The method of claim 5, wherein said therapeutic composition is dispensed from a hollow blade which also cuts said channel.

14. The method of claim 1, further comprising implanting a sustained release composition within said evacuated capsule.

15. The method of claim 14, wherein said sustained release composition comprises colloidal chromic phosphate P-32.

16. The method of claim 1, further comprising:
   inserting a radiation wand within the evacuated capsule, said radiation wand having a radiation emitting portion;
   inflating a balloon within said evacuated capsule to facilitate centering said radiation emitting portion within said evacuated capsule; and
   emitting radiation from said centered radiation emitting portion of said radiation wand.

17. The method of claim 16, wherein said balloon is inflated with a radiation filtering fluid composition.

18. The method of claim 17, wherein said radiation filtering fluid composition comprises a colloidal suspension of copper effective to absorb undesirable x-ray energies and re-radiate characteristic copper x-rays in all directions.

19. The method of claim 1, further comprising injecting said evacuated capsule with an aesthetic composition to preserve or enhance tissue volume and contour.

20. The method of claim 19, wherein said tissue is breast tissue.

21. The method of claim 1, wherein said operation is a breast reduction.

* * * * *